US010799762B2

(12) United States Patent
Clark et al.

(10) Patent No.: US 10,799,762 B2
(45) Date of Patent: Oct. 13, 2020

(54) TRAINING SCRIPTS

(71) Applicant: NIKE, Inc., Beaverton, OR (US)

(72) Inventors: James W. Clark, Portland, OR (US); Theodore H. Helprin, Portland, OR (US); Albert Shum, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 408 days.

(21) Appl. No.: 15/341,290

(22) Filed: Nov. 2, 2016

(65) Prior Publication Data

US 2017/0136300 A1 May 18, 2017

Related U.S. Application Data

(60) Continuation of application No. 14/691,211, filed on Apr. 20, 2015, now Pat. No. 9,511,261, which is a
(Continued)

(51) Int. Cl.
*G16H 20/30* (2018.01)
*G09B 5/02* (2006.01)
(Continued)

(52) U.S. Cl.
CPC .......... *A63B 24/0075* (2013.01); *A61B 5/021* (2013.01); *A61B 5/02438* (2013.01);
(Continued)

(58) Field of Classification Search
CPC . A63B 24/0075; A63B 71/0619; A63B 24/00; A63B 69/00; A63B 2071/0663;
(Continued)

(56) References Cited

U.S. PATENT DOCUMENTS

| | | | |
|---|---|---|---|
| 4,571,682 A | 2/1986 | Silverman et al. | |
| 4,776,583 A | 10/1988 | Jennings | |

(Continued)

FOREIGN PATENT DOCUMENTS

| | | |
|---|---|---|
| DE | 19955720 C2 | 4/2002 |
| EA | 1101511 A2 | 5/2001 |
| WO | 0239363 A1 | 5/2002 |

OTHER PUBLICATIONS

Internet Archive's Wayback Machine web captures of POLAR website downloaded Jan. 3, 2017 through Mar. 3, 2017 for (1) "Availability of the new Polar S-series" from http://web.archive/web/20020202031014/http://www.polar.fi/dld4tIBQGof2.html; (2) "The only training secret you'll ever need" from http://web.archive.org/web/20020203110253/ http://www.polar.fi/productfinder/serious/; (3) PolarS710—Advanced monitoring and memory features for the serious cyclist or multisport enthusiast: from http://web.archive.org/web/20020804143850/http://www.polar.fi/productfinder/serious/s710.shtml.
(Continued)

*Primary Examiner* — Sundhara M Ganesan
(74) *Attorney, Agent, or Firm* — Azuka C. Dike

(57) ABSTRACT

A training script device is described that conveniently allows a user to create a training script defining one or more steps of a workout routine, where each step may include an activity, a duration for performing that activity, and an intensity at which the activity is to be performed. Further, one or more steps of the training script can be self-starting in response to performance data detected by sensors of training script device executing the training script. This conveniently frees the athlete from having to continuously monitor the status of his or her workout activities. Still further, the training script device conveniently allows a user
(Continued)

to transfer training scripts to other training script devices, so that athletes can share successful training scripts.

13 Claims, 27 Drawing Sheets

Related U.S. Application Data continuation of application No. 14/490,283, filed on Sep. 18, 2014, now Pat. No. 9,039,572, which is a division of application No. 13/614,435, filed on Sep. 13, 2012, now Pat. No. 8,858,398, which is a continuation of application No. 13/455,950, filed on Apr. 25, 2012, now Pat. No. 8,287,436, which is a continuation of application No. 13/080,407, filed on Apr. 5, 2011, now Pat. No. 8,187,154, which is a division of application No. 10/413,366, filed on Apr. 15, 2003, now Pat. No. 7,946,959.

(60) Provisional application No. 60/386,210, filed on May 30, 2002.

(51) Int. Cl.
| | |
|---|---|
| G09B 19/00 | (2006.01) |
| G06Q 10/10 | (2012.01) |
| G06Q 10/06 | (2012.01) |
| G09B 23/30 | (2006.01) |
| H04L 29/08 | (2006.01) |
| A63B 24/00 | (2006.01) |
| A61B 5/021 | (2006.01) |
| A61B 5/024 | (2006.01) |
| A61B 5/11 | (2006.01) |
| A61B 5/00 | (2006.01) |
| A63B 69/00 | (2006.01) |
| A63B 71/06 | (2006.01) |
| A61B 5/145 | (2006.01) |

(52) U.S. Cl.
CPC ........... *A61B 5/1112* (2013.01); *A61B 5/1118* (2013.01); *A61B 5/486* (2013.01); *A61B 5/681* (2013.01); *A63B 24/00* (2013.01); *A63B 69/00* (2013.01); *A63B 71/0619* (2013.01); *G06Q 10/06311* (2013.01); *G06Q 10/109* (2013.01); *G09B 5/02* (2013.01); *G09B 19/00* (2013.01); *G09B 19/0038* (2013.01); *G09B 23/303* (2013.01); *G16H 20/30* (2018.01); *A61B 5/145* (2013.01); *A61B 2503/10* (2013.01); *A61B 2562/0219* (2013.01); *A63B 2024/0078* (2013.01); *A63B 2071/0663* (2013.01); *A63B 2220/12* (2013.01); *A63B 2220/17* (2013.01); *A63B 2220/34* (2013.01); *A63B 2220/40* (2013.01); *A63B 2225/20* (2013.01); *A63B 2225/50* (2013.01); *A63B 2230/04* (2013.01); *A63B 2230/207* (2013.01); *A63B 2230/30* (2013.01); *A63B 2230/50* (2013.01); *H04L 67/306* (2013.01); *Y10S 482/901* (2013.01)

(58) Field of Classification Search
CPC ............ A63B 2220/12; A63B 2230/50; A63B 2024/0078; A63B 2220/17; A63B 2220/34; A63B 2220/40; A63B 2225/20; A63B 2225/50; A63B 2230/04; A63B 2230/207; A63B 2230/30; G06Q 10/109; G06Q 10/06311; G09B 23/303; G09B 19/00; G09B 5/02; G09B 19/0038; A61B 5/1118; A61B 5/486; A61B 5/021; A61B 5/02438; A61B 5/1112; A61B 5/681; A61B 2503/10; A61B 5/145; A61B 2562/0219; G16H 20/30; H04L 67/306; H04L 2503/10; Y10S 482/901; G06F 19/3481

See application file for complete search history.

(56) References Cited

U.S. PATENT DOCUMENTS

| | | | |
|---|---|---|---|
| 4,828,257 A | 5/1989 | Dyer et al. | |
| 4,867,442 A | 9/1989 | Matthews | |
| 4,919,418 A | 4/1990 | Miller | |
| 5,089,960 A | 2/1992 | Sweeney, Jr. | |
| 5,213,555 A | 5/1993 | Hood et al. | |
| 5,215,468 A | 6/1993 | Lauffer et al. | |
| 5,387,164 A * | 2/1995 | Brown, Jr. | A63B 24/00 482/8 |
| 5,410,472 A * | 4/1995 | Anderson | A63B 21/00181 482/9 |
| 5,466,200 A | 11/1995 | Ulrich et al. | |
| 5,547,439 A | 8/1996 | Rawls et al. | |
| 5,645,509 A | 7/1997 | Brewer et al. | |
| 5,655,997 A | 8/1997 | Greenberg et al. | |
| 5,759,043 A | 6/1998 | Craig | |
| 5,785,632 A | 7/1998 | Greenberg et al. | |
| 5,799,652 A | 9/1998 | Kotliar | |
| 5,857,939 A | 1/1999 | Kaufman | |
| 5,890,995 A | 4/1999 | Bobick et al. | |
| 5,890,997 A | 4/1999 | Roth | |
| 5,899,963 A | 5/1999 | Hutchings | |
| 5,904,639 A | 5/1999 | Smyser et al. | |
| 5,916,063 A | 6/1999 | Alessandri | |
| 5,921,891 A | 7/1999 | Browne | |
| 5,931,763 A * | 8/1999 | Alessandri | A63B 24/0075 482/4 |
| 5,989,157 A | 11/1999 | Walton | |
| 6,013,007 A | 1/2000 | Root et al. | |
| 6,027,428 A | 2/2000 | Thomas et al. | |
| 6,050,924 A | 4/2000 | Shea | |
| 6,058,932 A | 5/2000 | Hughes | |
| 6,059,576 A | 5/2000 | Brann | |
| 6,059,692 A | 5/2000 | Hickman | |
| 6,066,075 A | 5/2000 | Poulton | |
| 6,188,927 B1 | 2/2001 | Lu et al. | |
| 6,287,239 B1 | 9/2001 | Hernandez | |
| 6,458,060 B1 | 10/2002 | Watterson et al. | |
| 6,464,618 B1 | 10/2002 | Shea | |
| 6,486,086 B1 * | 11/2002 | Kuznicki | B01D 53/228 502/208 |
| 6,626,803 B1 | 9/2003 | Oglesby et al. | |
| 6,638,198 B1 | 10/2003 | Shea | |
| 6,702,720 B2 | 3/2004 | Dardik | |
| 6,736,759 B1 | 5/2004 | Stubbs et al. | |
| 6,749,537 B1 | 6/2004 | Hickman | |
| 6,765,726 B2 | 7/2004 | French et al. | |
| 6,921,351 B1 | 7/2005 | Hickman et al. | |
| 8,298,123 B2 | 10/2012 | Hickman | |
| 2002/0033753 A1 * | 3/2002 | Imbo | G06Q 10/10 340/7.48 |
| 2002/0055419 A1 * | 5/2002 | Hinnebusch | G09B 19/003 482/8 |
| 2002/0059044 A1 | 5/2002 | Flentov et al. | |
| 2002/0133378 A1 * | 9/2002 | Mault | A61B 5/0002 705/3 |
| 2003/0017914 A1 * | 1/2003 | Jackowski | A63B 21/00 482/9 |
| 2003/0027688 A1 * | 2/2003 | Gordon | A63B 24/00 482/9 |
| 2003/0036683 A1 * | 2/2003 | Kehr | G06F 19/325 600/300 |
| 2004/0102931 A1 | 5/2004 | Ellis et al. | |
| 2009/0258758 A1 | 10/2009 | Hickman et al. | |

OTHER PUBLICATIONS (TM) H Polar et al; "User's Manual Quick Guide", Apr. 23, 2001 (Apr. 23, 2001), XP055387153, Retrieved from the Internet: URL:http://

(56) References Cited

OTHER PUBLICATIONS support.polar.com/support_files/en/C225742500419A8A422569f4004AA2FgG/179291_S710_GBRB.pdf.

"Heath Care, High-Tech Style", by Bernard Wyskocki, Jr., The Wall Street Journal, Apr. 17, 2001, 2 pages.

Printout of Web page (Netpulse Frequent Fitness Program), dated Dec. 3, 1999, 3 pages.

Printout of Web page from Interactive Fitness Technologies, Inc. (UltraCoach Standard), dated Nov. 30, 1999, 3 pages.

Printout of Web page from Interactive Fitness Technologies, Inc. (UltraCoach Multi-Sport Training Software Products catalog), dated Sep. 1999, 12 pages.

Printout of Web page from Interactive Fitness Technologies, Inc. (UltraCoach VR: How it Works?), dated Nov. 30, 1999, 2 pages.

Printout of Web page from Interactive Fitness Technologies, Inc. (UltraCoach VR Features), dated Nov. 30, 1999, 3 pages.

Printout of Web page from Interactive Fitness Technologies, Inc. (UltraCoach Fit Software Comparisons), dated Nov. 30, 1999, 2 pages.

Printout of Web page from Interactive Fitness Technologies, Inc. (UltraCoach Home Page), dated Nov. 30, 1999, 2 pages.

Mar. 16, 2011—(EP) ESR—App. No. 10197484.8.

\* cited by examiner

TRAINING SCRIPTS

RELATED APPLICATIONS

This application is a continuation of U.S. patent application Ser. No. 14/691,211 filed Apr. 20, 2015, which is a continuation of U.S. patent application Ser. No. 14/490,283 filed Sep. 18, 2014, now U.S. Pat. No. 9,039,572 issued May 26, 2015, which is a divisional of U.S. patent application Ser. No. 13/614,435 filed Sep. 13, 2012, now U.S. Pat. No. 8,858,398 issued Oct. 14, 2014, which is a continuation of U.S. patent application Ser. No. 13/455,950 filed Apr. 25, 2012, now U.S. Pat. No. 8,287,436 issued Oct. 16, 2012, which is a continuation of U.S. patent application Ser. No. 13/080,407 filed Apr. 5, 2011, now U.S. Pat. No. 8,187,154 issued May 29, 2012, which is a divisional of U.S. patent application Ser. No. 10/413,366 filed Apr. 15, 2003, now U.S. Pat. No. 7,946,959 issued May 24, 2011, which claims priority to provisional U.S. Patent Application No. 60/386,210 filed May 30, 2002, the content of each of which is expressly incorporated herein by reference in its entirety.

FIELD OF THE INVENTION

The invention relates to a workout script for providing a user with workout instructions based upon characteristics of the user during the workout, or upon characteristics of the workout itself. For example, a workout script may instruct a user to run until the user's heart rate reaches 80 beats per minute, and then subsequently instruct the user to stretch for a cooling-off period of ten minutes. Alternately, a script may instruct a user to run for a predetermined distance or for a predetermined period of time, and then instruct the user to take another action after the distance has been run or the period of time has expired. Still further, the invention relates to the creation and use of such workout scripts.

BACKGROUND OF THE INVENTION

There has been a steadily growing interest in fitness, both for health reasons and for personal development. As the popularity of various physical fitness activities has grown, people have become more interested in achieving specific goals through these activities. For example, some people take up exercise to lose weight, others to participate in a particular type of sport, such as soccer or marathon racing, and still others just to gradually improve their overall physical condition. Correspondingly, a great deal of scientific research has been conducted as to how people may reach these specific goals. For example, some scientific research has indicated that the fastest way for someone to lose fat through exercise is to exercise such that the person's heart rate is maintained within a specific range or "zone" of beats per minute.

This research should ideally allow people of all walks of life to maximize the results obtained from their fitness activities. In practice, however, few people can take advantage of this research. While an athlete may create a schedule of fitness activities or training routine designed to obtain specific results through one or more physical activities, he or she will probably have difficulty following that training routine while actually engaged in those physical activities.

For example, an optimized group of physical activities or "workout" may call for an athlete to run until his or her heart rate is within a desired heart rate zone (that is, a percentage range of his or her maximum heart rate), and then switch to another, less strenuous activity, such as jogging or stretching, after ten minutes. While running, however, that athlete cannot easily determine when his or her heart rate reaches the targeted zone. Even if he or she employs a heart rate monitor to measure his or her heart rate, the athlete must continuously watch the heart rate monitor to ascertain when his or her heart rate reaches the desired zone. The athlete must then initiate a timer to measure how long his or her heart rate remains within the desired zone.

This module requires significant concentration that detracts from the workout itself. Thus, users will commonly not adhere to a training routine, or, alternatively, will not prepare a detailed training routine that maximizes the results of their workout. Accordingly, there is a need for a method and apparatus that will allow a person to create a training routine scheduling each part or step of a workout, determine when the requirements of a particular step have been fulfilled, and then prompt the user to begin the subsequent step of the workout.

BRIEF SUMMARY OF THE INVENTION

Advantageously, the invention allows a user to create a training script for a workout. That is, the invention allows a user to create a set of instructions that defines a series of activities to be performed during a workout, and a quantity associated with at least one of the activities. When executed, the instructions prompt a device to sequentially display each activity until the athlete has performed the defined quantity associated with that activity, and then to display the next activity. The device may further allow a user to electronically share created training scripts with others.

Still further, the invention may include a device that displays a physical activity listed in an electronic training script to a user. The device then detects at least one characteristic of the user's workout associated with a quantity defined in the training script for that physical activity. When the device detects that the workout characteristic matches the defined quantity, the device then displays the next activity subsequently listed in the electronic training script. Thus, the invention provides a way for a user to design a precise training routine, and then to be timely prompted to follow the training routine. Further, the invention allows a user to share a successful training routine with others. These and other features of the invention will become apparent based upon the following description of the invention with reference to associated drawings.

DETAILED DESCRIPTION OF THE INVENTION

Overview

The invention allows a user to create a training script for a workout. A training script is a group of one or more training steps corresponding to different portions of a workout. Each training step includes instructions to be executed by a computing device. These instructions define an action, such as a physical activity to be performed during a workout, and a quantity associated with that action. When executed by a computing device, the instructions command the computing device to display a prompt for the user to perform the action, until the device receives performance data indicating that the user has performed the quantity designated for the action. The device then executes the next sequential training step. Using these instructions, the device will sequentially display a prompt for the user to perform each action in a workout, until the user performs the designated quantity for each of the actions.

According to various embodiments of the invention, the quantity for performing an action can be the duration of the action itself. For example, the duration may be the time period for which the action is to be performed. Alternately, the duration may be a distance to be traversed by performing the action. A training step may thus call for an athlete to run for the duration of five miles. Still further, the duration may be the number of times that an action should be repeated, or an amount of work exerted while performing the action. A training step could, for example, call for an athlete to repeat a weight-lifting exercise 20 times, or jog until the athlete has burned 600 calories.

A step may also specify a quantity for performing an action that is based upon an intensity associated with that action. The intensity of an action may be defined by any desired unit, such as the heart rate experienced by the user while performing the action. The intensity may also be, for example, a pace at which the action is performed, or an amount of force created while performing the action. Still further, a step may include a quantity specifying both an intensity and a duration. Thus, a step may call for a biker to bike at a force of 200 dynes for 35 minutes. Of course, still other units of measurement can be used to define a quantity for performing an action, such as a user's blood oxygen level or blood pressure level.

General Computing Device

Figure 1:
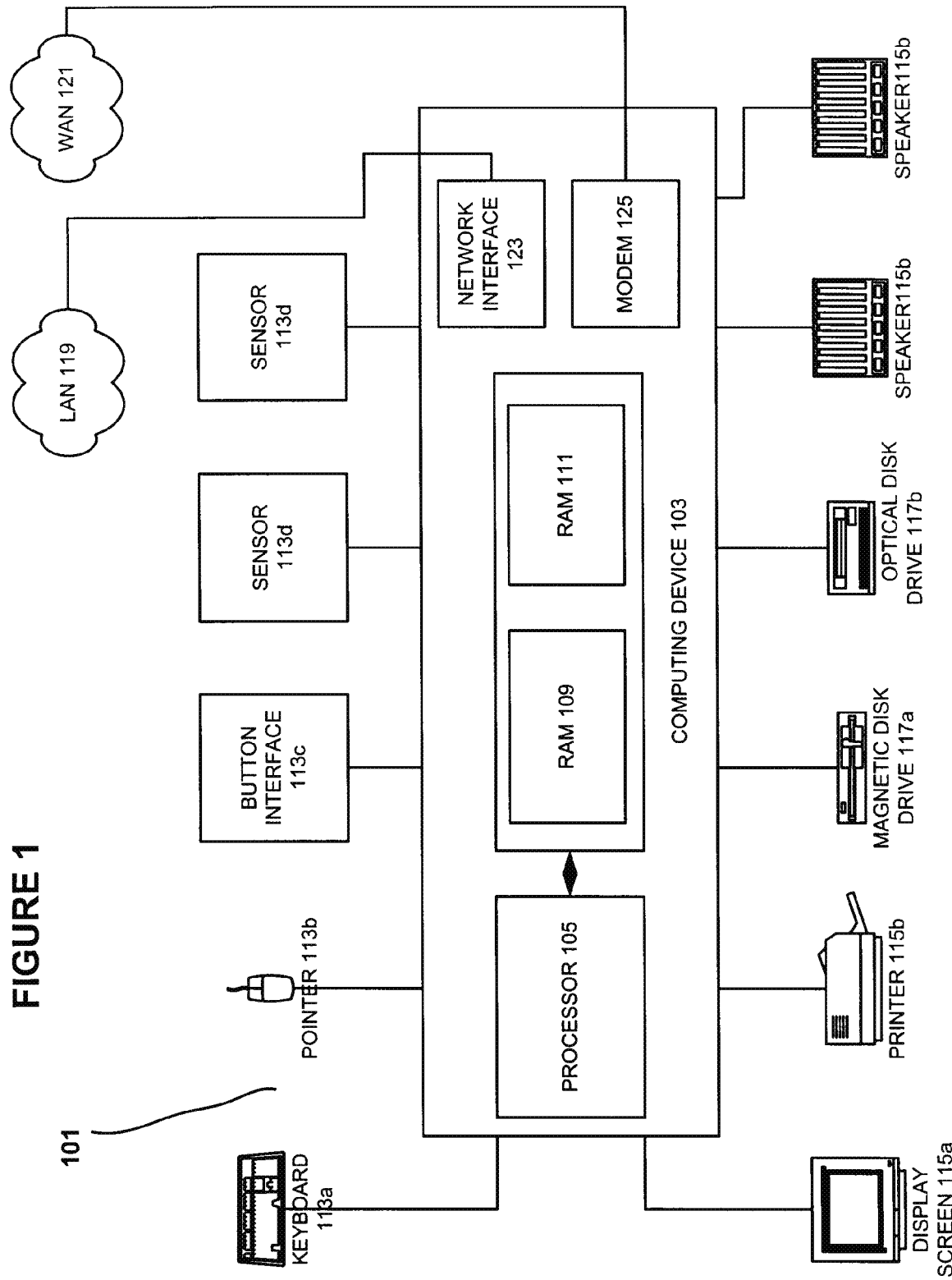
FIG. 1 shows a generic computing device that can be used for creating a training script or for implementing a training script according to an embodiment of the invention.

Various embodiments of the invention may conveniently be implemented on a general-purpose computing device, such as a desktop personal computer, a laptop computer, or a personal digital assistant (PDA), or on a special-purpose computing device, such as a digital wristwatch. Referring now to FIG. 1, this figure illustrates an exemplary general-purpose computer device that can be used to implement various aspects of the invention. In FIG. 1, the computer device 101 has a computer 103 that includes a processor 105, such as a programmable microprocessor, and a system memory 107 coupled to the processor 105. The system memory 107 may be implemented using any appropriate memory devices, such as one or more microcircuit devices. The system memory 107 will typically include both a read only memory (ROM) 109 and a random access memory (RAM) 111. The ROM 109 and RAM 111 may be connected to the processor 105 using a conventional bus structure (not shown), such as a memory bus or memory controller, a peripheral bus, and a local bus using any of a variety of bus architectures.

The computer device 101 will also include one or more input devices 113. For example, if the computer device 101 is a conventional desktop computer or laptop computer, it may include a keyboard 113a, and a pointing device 113b, such as a mouse or touchpad. Further, the computer device 101 may include additional or alternate input devices 113, such as a microphone, a pointing stick, or a digitizer for accepting input through a stylus. If the computer device 101 is a special-purpose computing device, such as a digital wristwatch, it may instead only have input devices suited for its particular purpose.

For example, rather than a large keyboard 113a or pointing device 113b, if the computer device 101 is a wristwatch it may instead include a button interface 113c having a small number of depressable buttons. It may also have one or more sensors 113d for measuring characteristics of the device's environment. Thus, the sensors 113d may include a heart rate monitor for measuring the heart rate of a person using the computer device 101, an accelerometer or pedometer for measuring the travel of a person using the computer device 101, a thermometer, an altimeter, a compass, a blood oxygen monitor for monitoring the blood oxygen content of a person using the computer device 101, or other measurement device. A sensor 113d may be included in the same casing as the computing device 103, or the sensor 113d may be remotely locating and transmit measured data to the computing device 103 using a wired or wireless medium.

The computer device 101 will also include one or more output devices 115, such as a display screen 115a, a printer 115b, and speakers 115c. For example, if the computer device 101 is a conventional desktop computer, then the display screen 115a may be a large CRT or flat panel monitor. Alternately, if the computer device 101 is a special-purpose computing device, it may only have the output devices 115 suited for its particular purpose. For example, if the computer device 101 is a digital wristwatch, display screen 115a may be a small LCD display, and the computer device 101 may have only one small speaker 115b and omit the printer 115c altogether. Of course, the computer device 101 may also include additional or alternate output devices 115 as desired.

Depending upon its configuration, the computer device 101 may also include one or more peripheral data storage devices 117. The computer device 101 may have, for example, a magnetic disk drive 117a for reading from and writing to a magnetic disk (such as a hard disk drive or a floppy disk drive), and an optical disk drive 117b for reading from or writing to a removable optical disk (such as a CD ROM or other optical media). Of course, the computer device 101 may also include other types of data storage devices 117, such as magnetic cassettes, flash memory cards, digital video disks, Bernoulli cartridges. Also, if the computer device 101 is a digital wristwatch, then the computer device 101 may include a small peripheral data storage device 117, such as a Memory Stick or a Secure Digital card.

As will be appreciated by those of ordinary skill in the art, the computer device 101 executes instructions stored in the system memory 107. These instructions may be retrieved to the system memory 107 from one or more of the peripheral storage devices. In addition, the computer device 101 may receive input data for executing the instructions from a user through the input devices 113. Similarly, the computer device 101 may output the results of executing the instructions to the user through the output devices 115.

Some computer devices 101 can operate in a network of other computer devices 101. The network may be, for example, a local area network (LAN) 119 or a wide area network (WAN) 121, such as the Internet. For connection to the local area network 119, the computer device 101 may include a network interface or adapter 123. For connection to the wide area network 121, the computer device may include a modem 125 or other means for establishing communications over the wide area network 121. Of course, it will be appreciated that the network connections shown are exemplary, and that other techniques for establishing a communications link with other computer devices 101 can be used. Further, those of ordinary skill in the art will appreciate that a variety of communication protocols may be used for exchanging data between computer devices 101, such as TCP/IP, Ethernet, FTP, HTTP.

System for Creating and Executing a Training Script

Figure 2:
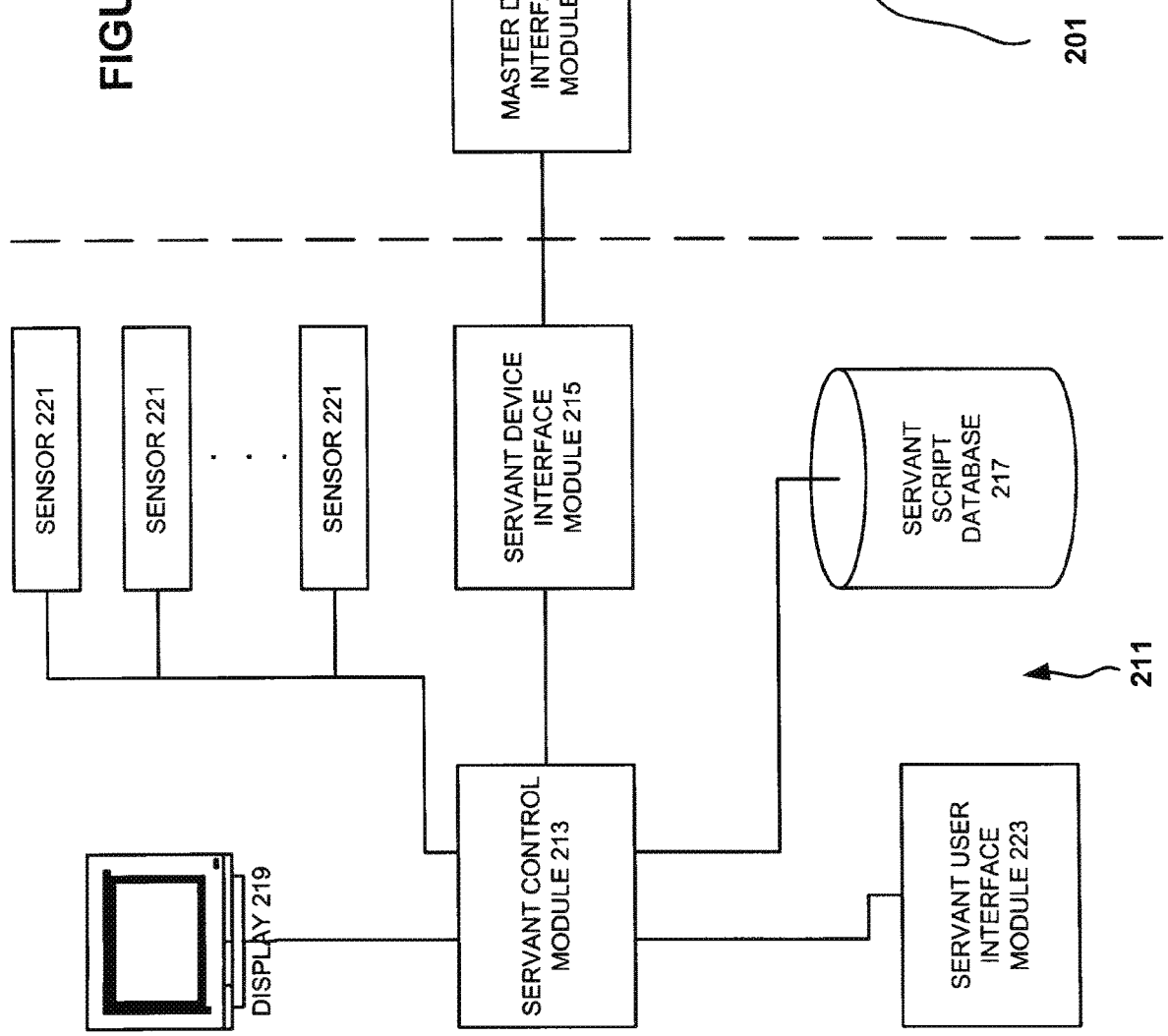
FIG. 2 shows a schematic diagram of a device for creating a training script and a device for implementing a training script according to an embodiment of the invention.

FIG. 2 illustrates a master device 201 for creating a training script, and a servant device 211 for implementing a training script. More particularly, a user employs the master device 201 to create instructions making up a training script, and the servant device 211 executes the instructions of the training script. As will be appreciated by those of ordinary skill in the art, the master device 201 may be a computer device 101 of the type described about, such as a desktop or laptop computer, implementing a software application for defining training scripts. Of course, with various embodiments of the invention, the master device 201 may instead be a hardware or firmware device for creating training scripts.

Once the user has created the training script, the script is transferred from the master device 201 to the servant device 211. With some embodiments of the invention, the servant device 211 may be a portable computer device 101 of the type described above that can be easily carried by an athlete during a workout. For example, the servant device 211 may be embodied as a wristwatch with one or more remote sensors for measuring various characteristics of the user's workout. Of course, the servant device 211 also may be implemented with other types of portable computer devices, such as personal digital assistants. Alternately, the servant device 211 may be implemented using hardware or firmware.

Device for Creating a Training Script

As seen in FIG. 2, the master device 201 includes a master control module 203, a master user interface module 205, a master device interface module 207, and a master script database 209. As will be discussed in detail below, for each step to be included in a training script, the master user interface module 205 prompts a user to input data specifying an action to be performed for that step. The master user interface module 205 also prompts the user to specify a quantity of the action to be performed. From the input data received through the master user interface module 205, the master control module 203 creates training steps for operating the servant device 211, and compiles the training steps into a training script file.

The master control module 203 then forwards the training script file to the master script database 209 for storage. As will be appreciated by those of ordinary skill in the art, the master script database 209 may be embodied using any suitable memory medium. The master script database 209, for example, may be implemented on a microcircuit random access memory, a magnetic disk drive, a writable optical disk drive or the like.

When the user desires to exercise using the created training script, the user instructs the master control module 203 to transfer the training script file from the master script database 209 to the master device interface module 207. The master device interface module 207 then provides the training script file to the servant device 211. As will be appreciated by those of ordinary skill in the art, the master device interface module 207 can be implemented using a variety of techniques. For example, the master device interface module 207 may employ a wireless communication device to communicate with the servant device 211, such as an infrared or radio frequency transmitter. Alternately, the master device interface module 207 may include a cable port for employing a hard-wired communication device to communicate with the servant device 211, such as an RS-232, USB or Firewire link.

With some embodiments of the invention, the master device interface module 207 or other interface module may allow the master device 201 to transmit training scripts files to and/or receive training script files from a variety of other devices in addition to the servant device 211, such as other computing devices 101 including, for example, other master devices 201. Again, the master device interface module 207 may employ any suitable communication protocol to transfer training script files from the master device interface module 207 to these other devices. It should be noted that training script files, like other electronic files, can be transferred from the master device 201 to other computer devices 101 using any known file transfer technique. For example, the master device 201 may be embodied by a personal computer that also supports electronic mailing protocols, such as the POP3 protocol. With this arrangement, a user can transfer a training script from the master device 201 to another computer device 101 using electronic mail. Also, protocols such as WiFi or Bluetooth for wireless communications can be used to wirelessly transmit training script files to other devices.

By allowing a user to transfer created training script files from the master device 201 to another computer device 101, athletes may easily and conveniently share successful training routines with each other. Rather than having to write down a particular training routine, an athlete can simply transfer the electronic training script file to another athlete using, for example, electronic mail. The athlete receiving the electronic training script file can then forward the file to his or her servant device 211, and exercise according to the routine defined by the training script file without ever having to examine or manually copy the workout routine defined by the training script.

Creating a Training Script

Figure 3:
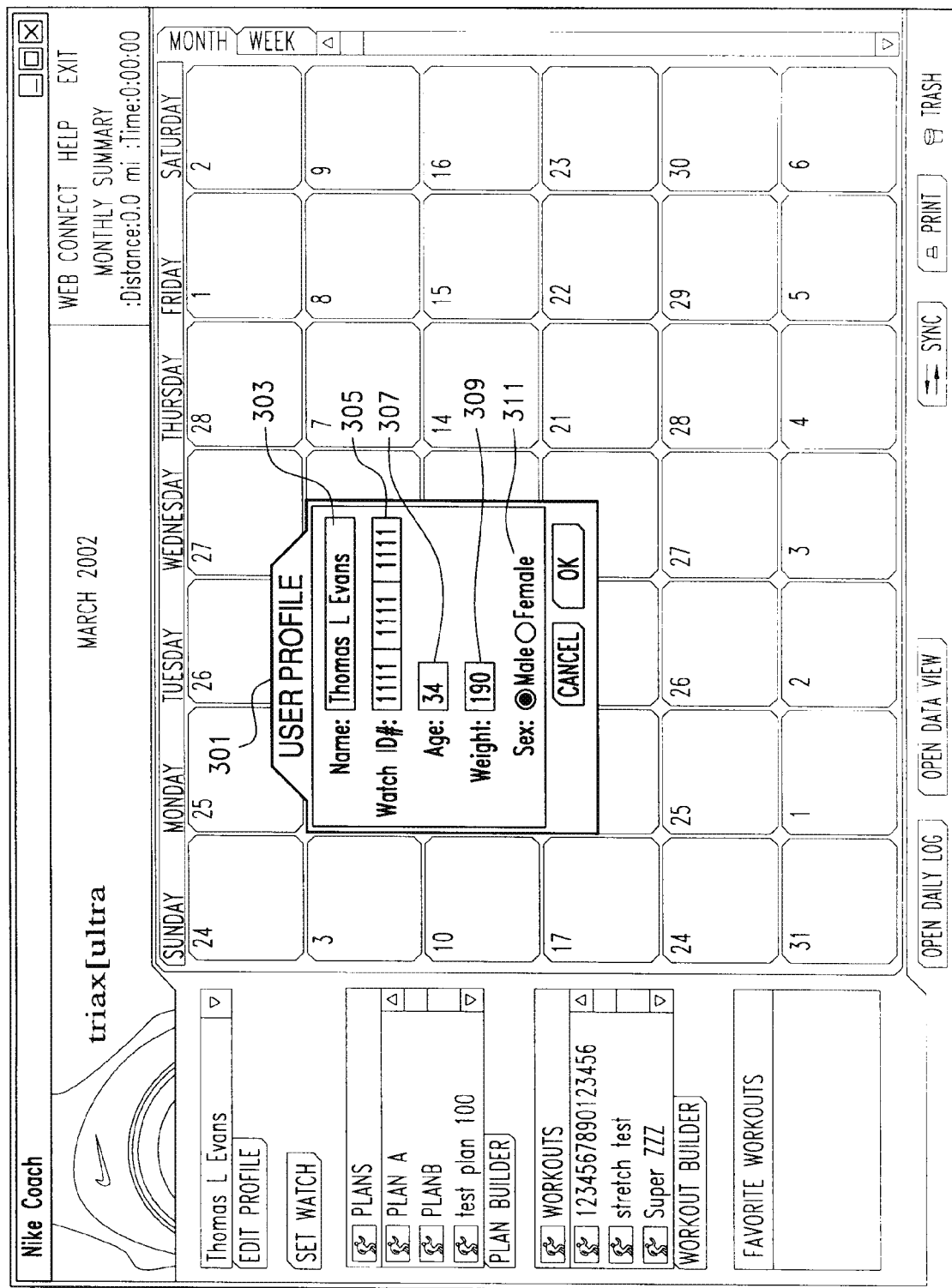
FIGS. 3, 4A, 4B, 5A-5P, 7A-7C and 9 show various user interfaces according to an embodiment of the invention.

FIG. 3 illustrates a first user interface 301 provided by the master user interface module 205 for creating a training script. The interface 301 includes a group of data fields that allow a user to define a user profile. As will be discussed below, defining a user profile allows a user to associate one or more workouts and a servant device 211 with a particular athlete. This conveniently allows more than one person to share the use of the master device 201 without confusing training script files between the users.

The interface 301 includes a name field 303 naming the profile. Thus, a user may enter his or her own name into the name field 303 to identify the user profile with that particular user. Each user profile includes a schedule of training scripts selected by the user. Each profile also contains a group of training script files, referred to as the "favorite workouts" group. A user may then add existing training script files to or delete training script files from this group of favorite training scripts. The favorite workouts group allows a user to avoid having to scroll through every training script created with or received by the master device 201 each time the user wants to use a particular script. Instead, the user can simply include his or her favorite training script in the "favorite workout" group for the user's profile, and select a desired script for use directly from this smaller group. As will be explained in detail below, when a user "synchronizes" the servant device 211 to the master device 201, both the training scripts in the "favorite workout" group and the scheduled training scripts are copied to the servant device 211.

In addition to the name field 303, the interface 301 also has a servant device identification field 305, which associates the user profile with a particular servant device 211. As noted above, a computer device 101 used to embody a servant device 211 may have one or more sensors 113*d* for measuring the characteristics of a user's activities. A training script may thus include instructions that are executed in response to the servant device 211 receiving data from a particular type of sensor 113*d*. Different servant devices 211 may have different types of sensors 113*d*, however, so a workout that may execute on one servant device 211 may not properly execute on a different servant device 211.

The value of the servant device identification field 305 can be used to address differences in servant devices by specifically identifying the user's servant device 211, and, by extension, the sensors 113*d* and other equipment included with the user's servant device 211.

For example, the master device 201 may include a table correlating servant device 211 identification values with one or more sensors 113*d*. Thus, when the user enters a value into the servant device identification field 305, the master device 201 can determine the sensors 113*d* employed by the user's servant device 211 from the table. Alternately, the master device 201 may use the value entered into the servant device identification field 305 to determine the sensors 113*d* available for use by the servant device 211 from a remote source, such as a database available over a network (e.g., the Internet). If the user's servant device 211 does not have a particular sensor 113*d* required by a training script, then the master device 201 may refrain from copying that training script to the user's servant device 211 during synchronization.

The interface 301 also includes age, weight and sex fields 307-311, respectively. The user may enter this information about himself or herself into these fields. Of course, with other embodiments of the invention, the interface 301 may include fields for additional user health information, or may omit any of fields 307-311 entirely.

Figure 4A:
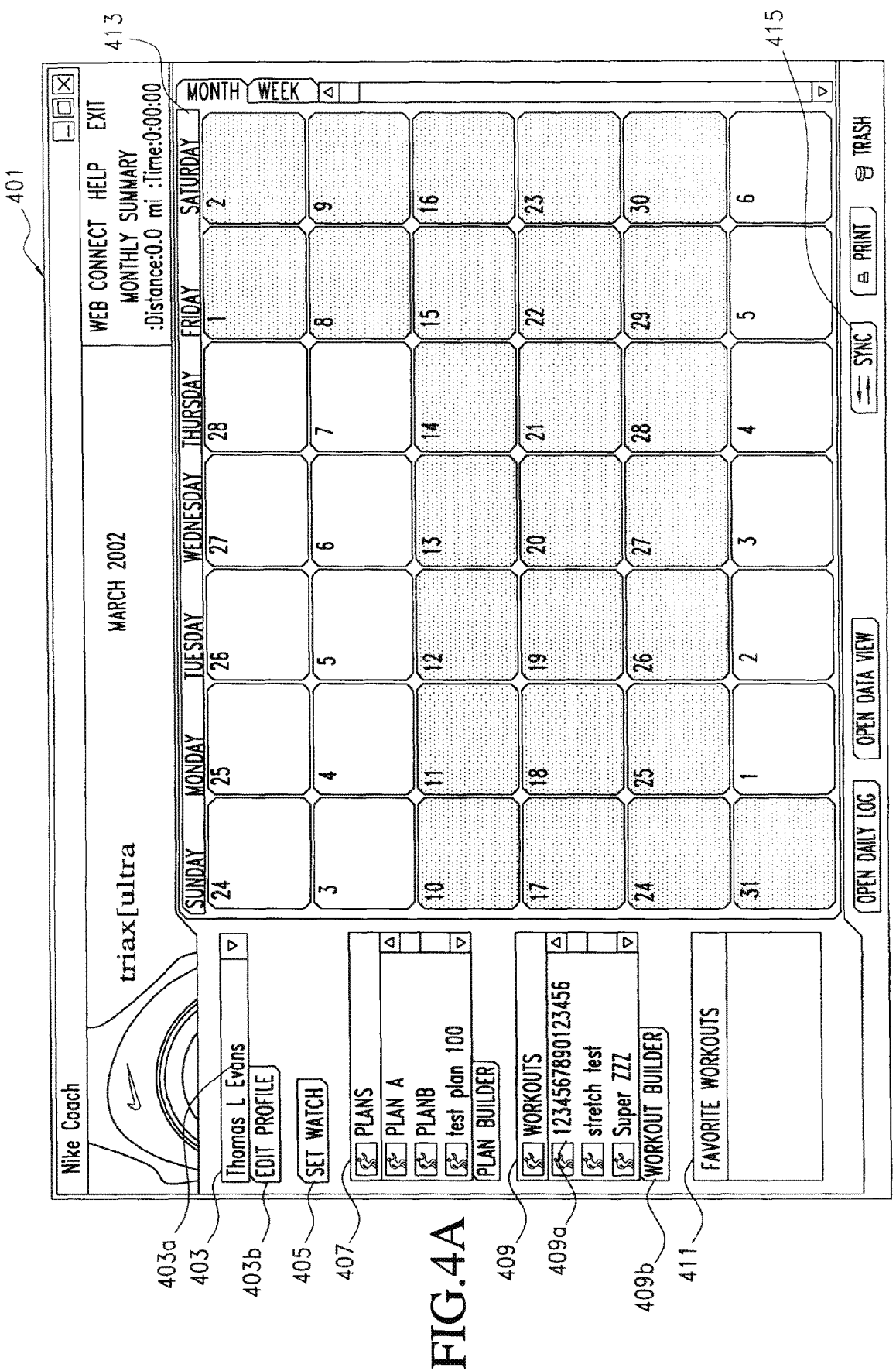

After the user has created a user profile by entering the relevant values into the interface 301, the master user interface module 207 displays interface 401 shown in FIG. 4A. This interface, which is the main user interface for creating and using training scripts, includes a user profile sub-interface 403, a set watch sub-interface 405, a plans sub-interface 407, a workout sub-interface 409, a favorite workouts sub-interface 411, and a calendar sub-interface 413. The user profile sub interface 403 includes a name field 403*a*, identifying the name of the currently selected user profile, and an edit button 403*b*, which, when activated, causes the master user interface module 207 to display the user interface 301. The set watch sub-interface 405 is a command button. As will be discussed in detail below, activating the command button 405 causes the master user interface module 207 to display a user interface for adjusting the settings of the associated servant device 211, which, in this embodiment, is a watch. The favorite workouts sub-interface 411 provides a listing of the training scripts the user has included in the favorite workouts group of the profile.

The workout sub-interface 409 includes a list 409*a* of previously created (or received) training scripts corresponding to individual workout routines. The workout sub-interface 409 also includes a workout builder command button 409*b* that allows a user to create a new training script. When a user activates the workout builder command button 409*b*, the master user interface module 207 provides the user with interface 501 shown in FIG. 5A. The operation of this interface will be explained with reference to FIGS. 5A-5P and to FIG. 6, which illustrates a flowchart showing how a training script can be created using the interface 501.

Figure 5A:
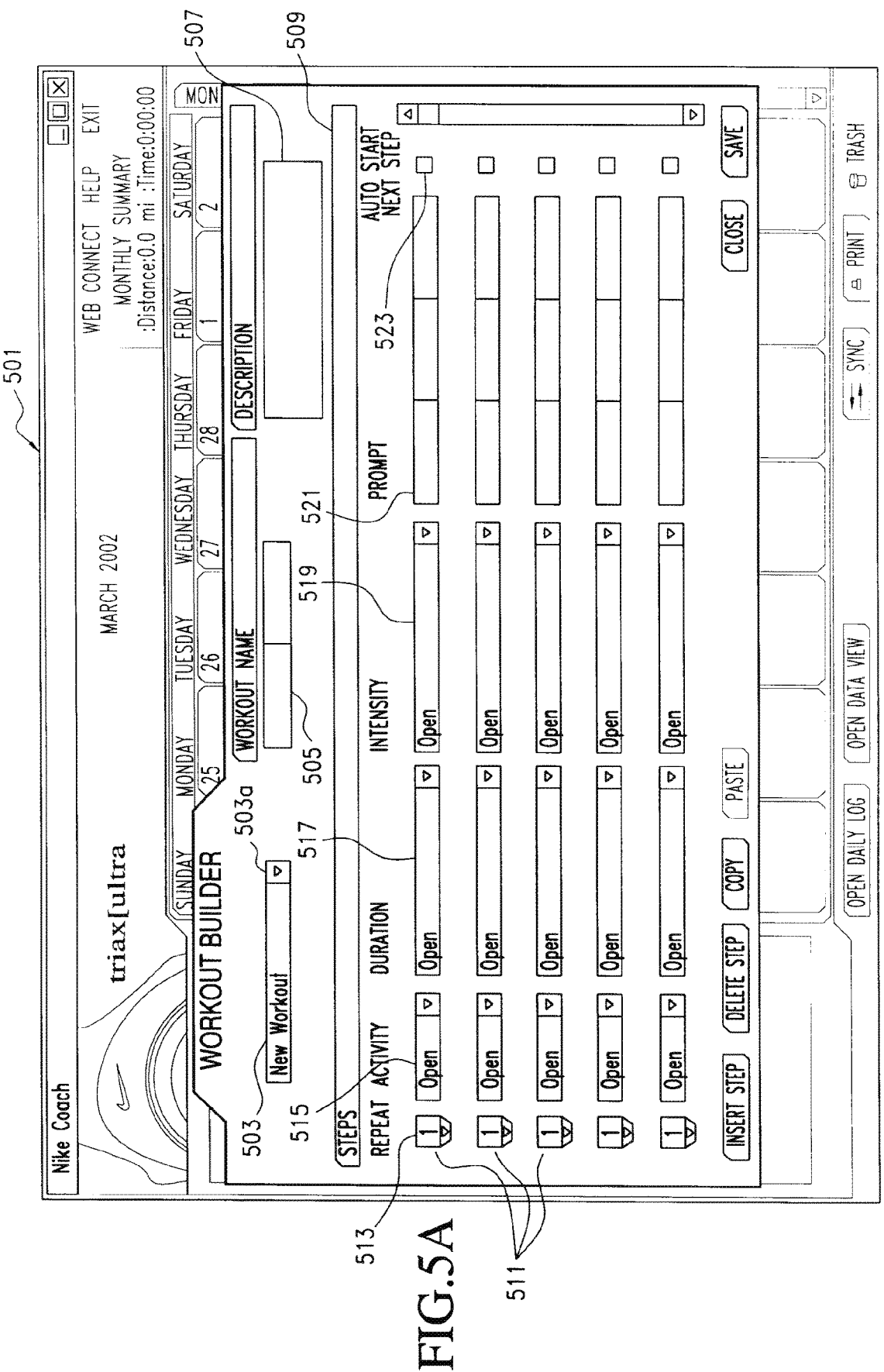
Figure 5B:
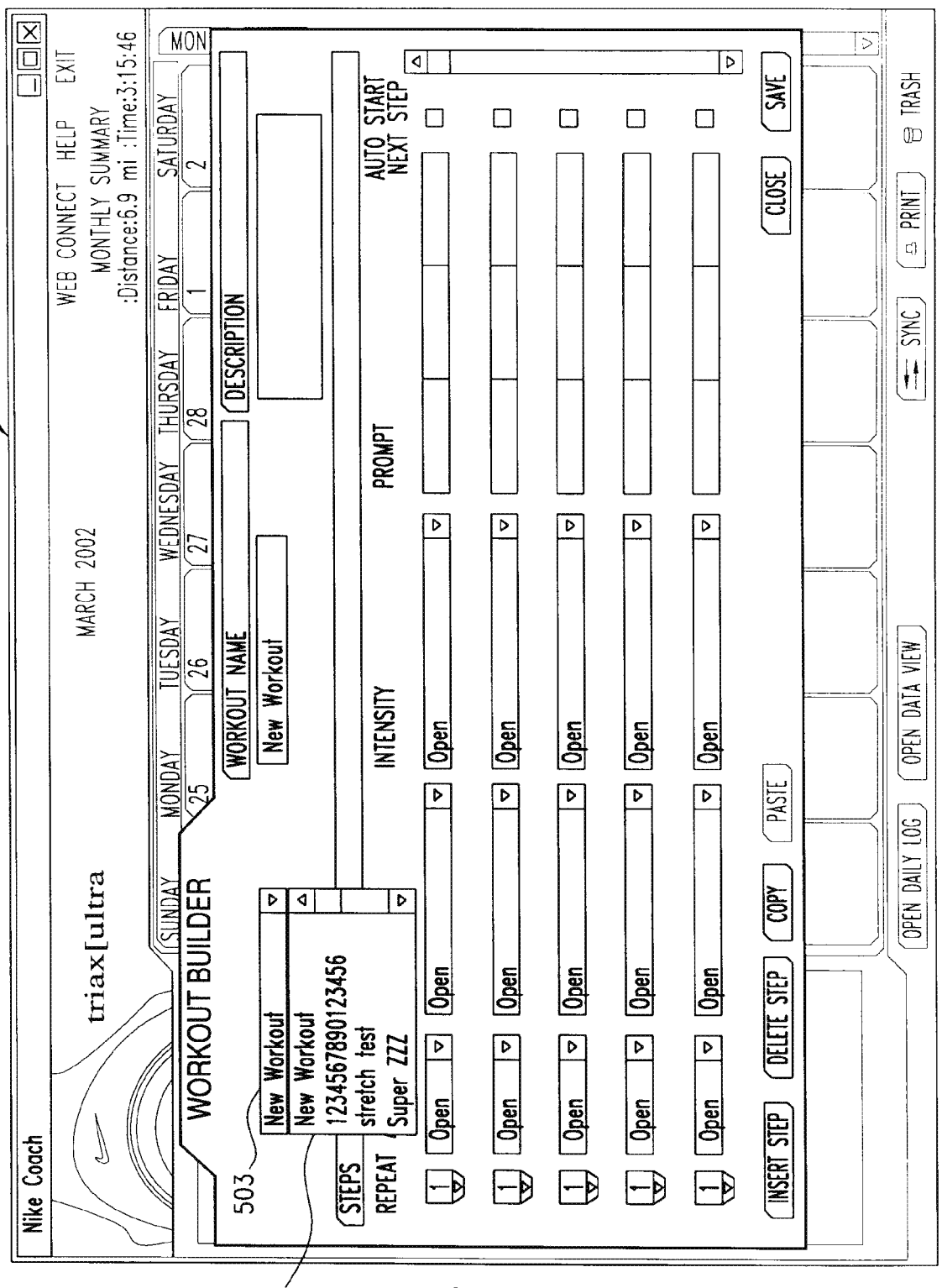
Figure 6:
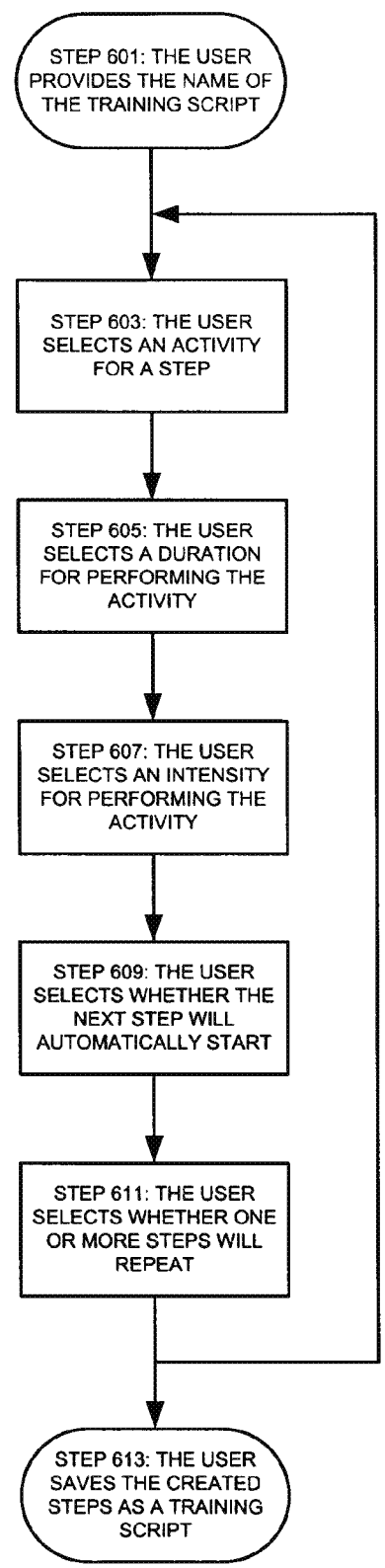
FIG. 6 illustrates a flow chart for creating a training script.

First, in step 601, the user enters the name of the training script into the workout selection field 503 of the interface 501. As will be appreciated by those of ordinary skill in the art, the workout selection field 503 provides a drop-down menu 503*a*, listing the previously created workout training scripts associated with the current user profile, as shown in FIG. 5B. Thus, if the user is going to edit a training script that already exists, the user simply selects the name of that training script from the drop-down menu 503*a*. If the user instead wishes to create a new workout training script, he or she selects the name "New Workout" from the drop down menu 503*a*. This selection ensures that the remaining fields in the display 501 are empty for the user to enter values, as shown in FIG. 5A.

Figure 5C:
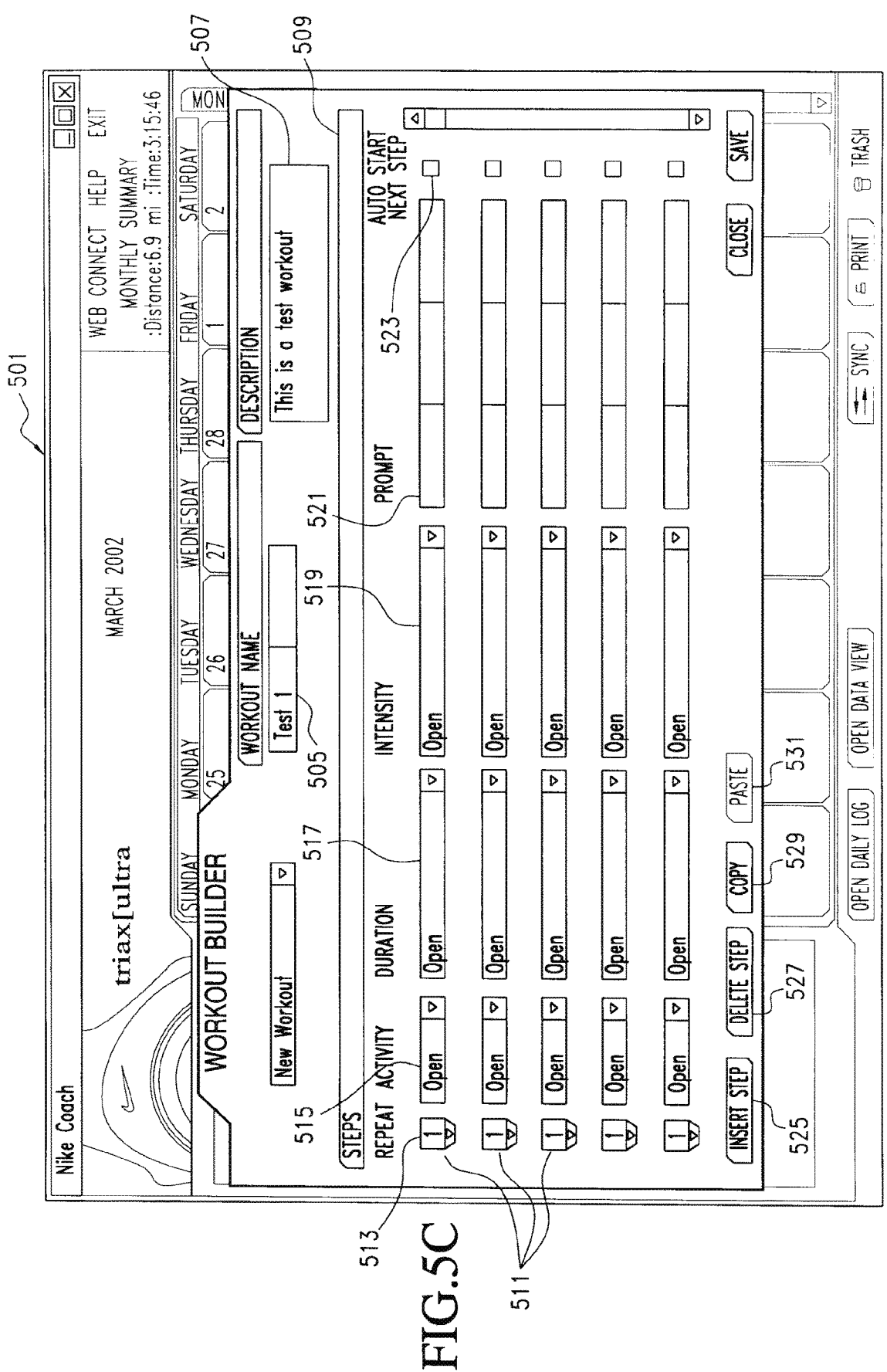

The interface 501 also includes a workout name field 505 and a description field 507. The workout name field 505 allows a user to create a name for the new workout training script, as shown in FIG. 5C. Providing a name for a workout training script conveniently allows it to be easily referenced later. As also seen in FIG. 5C, the description field 507 can contain a brief description of the workout training script, such as an identification of its purpose or difficulty.

The interface 501 further includes a steps interface 509 (referred to by the title "STEPS" in the figure). The steps interface 509 includes a plurality of step sub-interfaces 511. Each step sub-interface 511 appears as a row of six fields 513-523. More particularly, as seen in FIG. 5A, each step sub-interface 511 includes a repeat field 513, an activity field 515, a duration field 517, an intensity field 519, a prompt field 521, and an auto start field 523. The function and operation of each of these fields 513-523 will be described in detail below. The steps interface 509 also includes edit buttons 525-531 for editing the arrangement of the step sub-interfaces 511. The function and use of these edit buttons 525-531 are well known in the art, and thus will not be discussed in detail here.

Figure 5D:
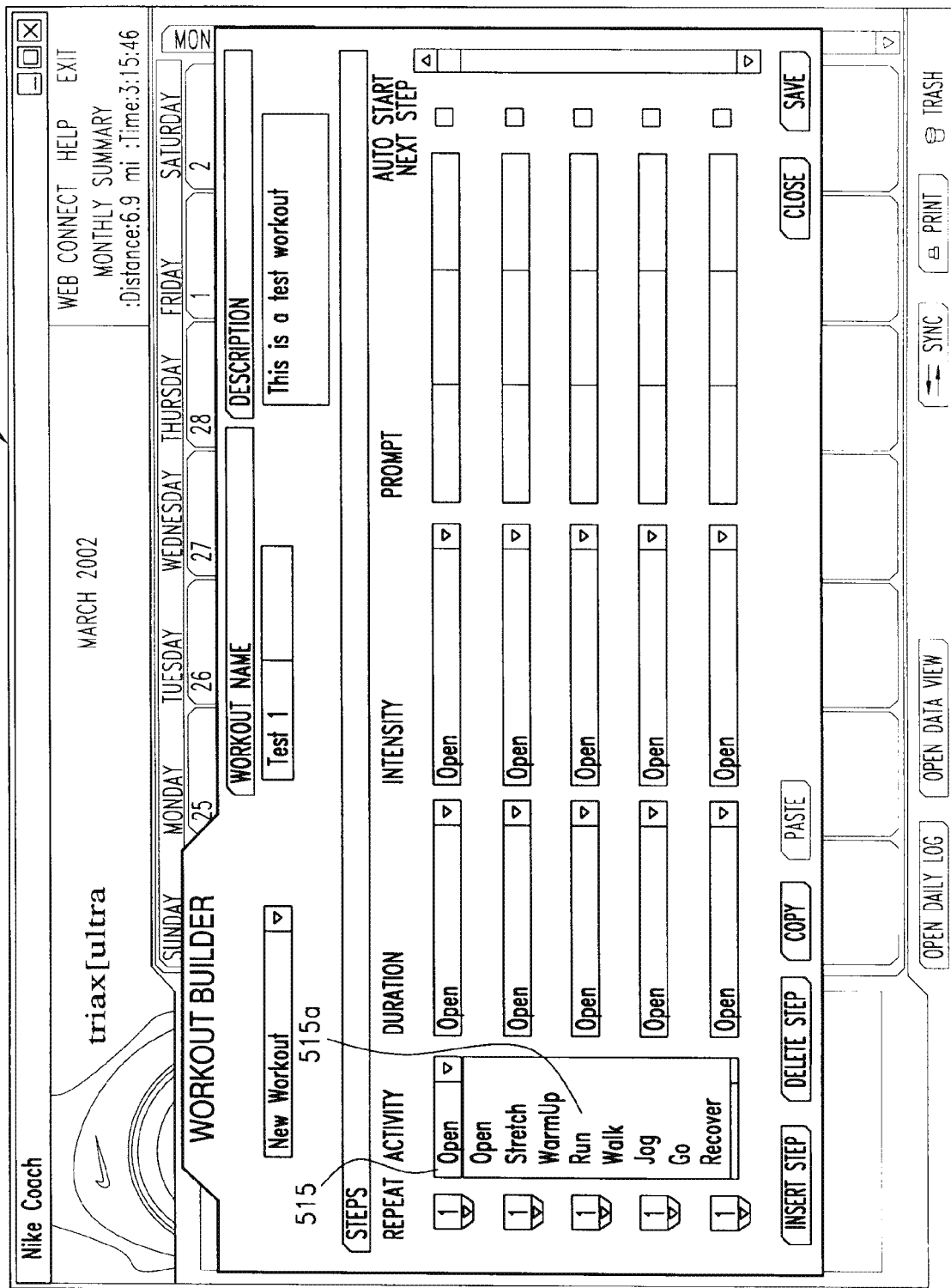

Turning first to the field 515, this field provides a drop-down menu 515*a* listing a variety of actions. For example, as seen in FIG. 5D, the drop-down menu 515*a* may include the actions "open" (that is, no specified activity), "stretch," "warm up," "run," "walk," "jog," "go," and "recover." Of course, it will be appreciated that other embodiments of the invention may list more, less or different activities. Using the drop-down menu 515*a*, in step 603 the user selects a particular activity to be displayed in the field 515. It should also be noted, however, that while the illustrated embodiment of the invention employs the drop-down menu 515*a* to select a value for the field 515, other embodiments of the invention may allow a user to enter a value directly into the field 515.

Figure 5E:
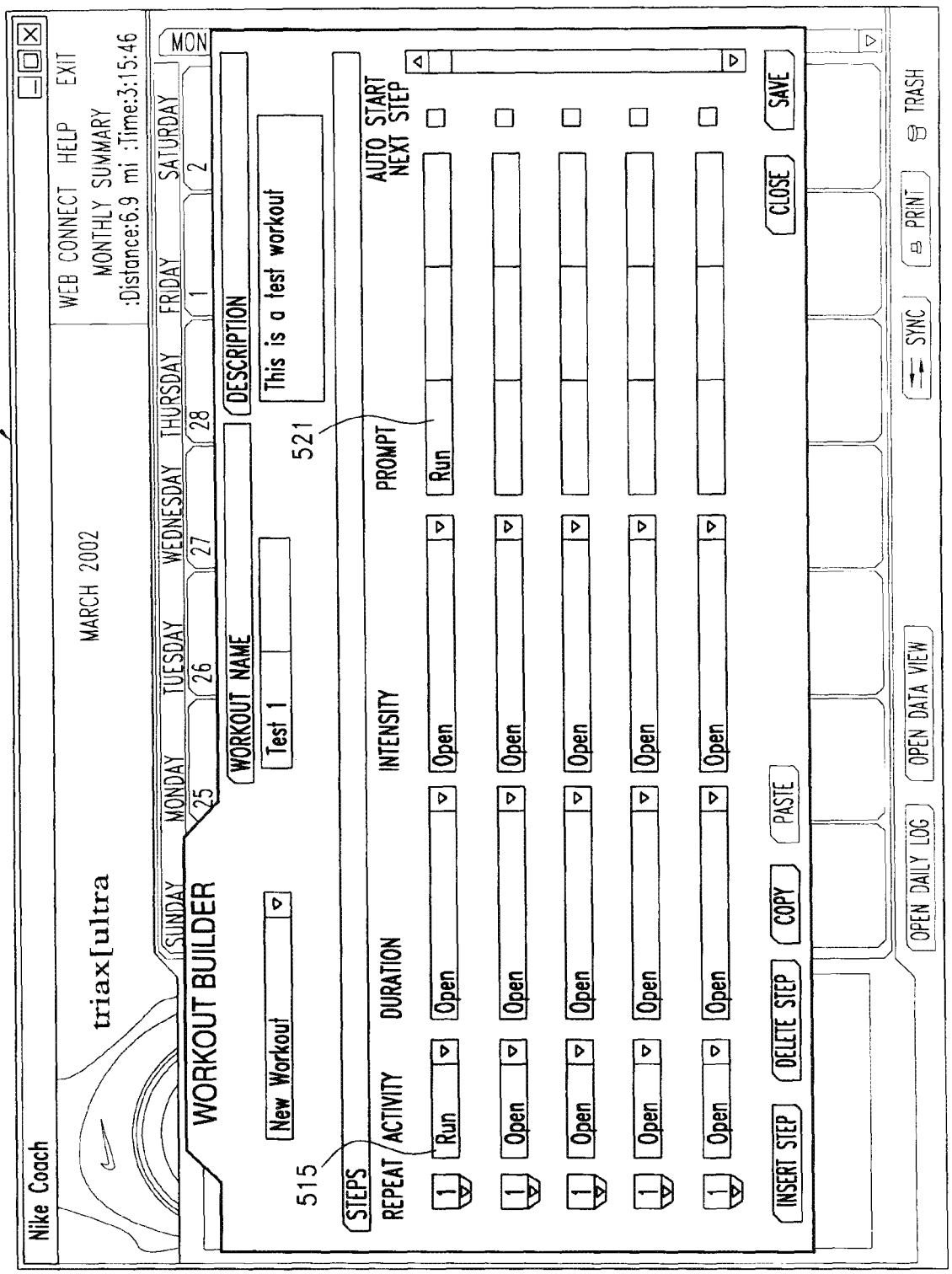

When the user selects the value of the field 515, this value is then added to the prompt field 521. The prompt field 521 for a step sub-interface 511 contains the information that will be displayed to a user when instructions corresponding to that step are later executed by a servant device 211. Thus, if the user selects the activity "run" for the field activity field 515, the word "run" is added to the prompt field 521, as seen in FIG. 5E. Of course, the display of the selected activity (or duration or intensity, as will be discussed below) in the prompt field 521 may be omitted with various embodiments of the invention. Further, as will be appreciated by those of ordinary skill in the art, some embodiments of the invention may omit the prompt fields 521 altogether.

Figure 5F:
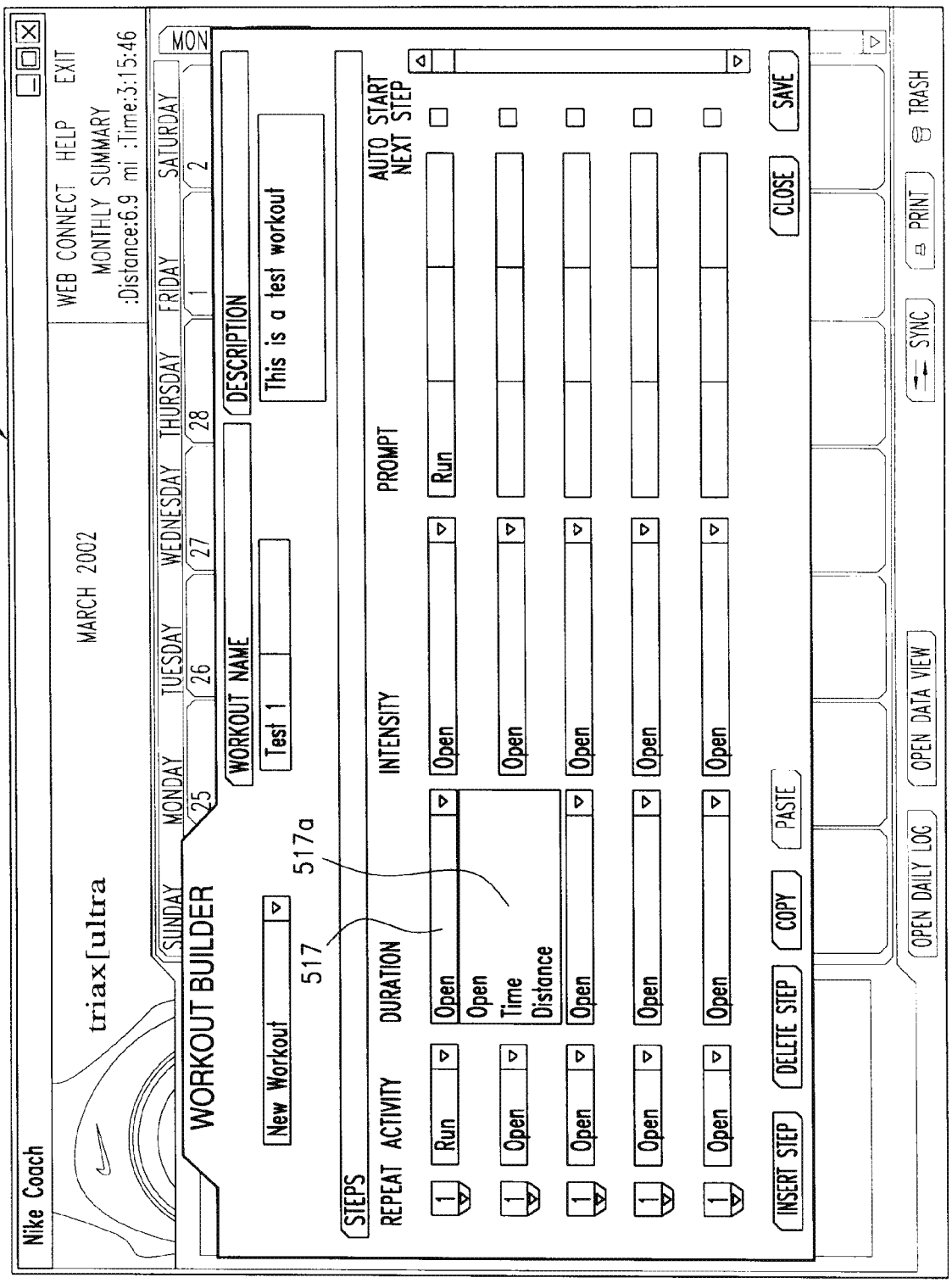

The duration field 517 in a step sub-interface 511 allows the user to select a duration for performing the activity designated in the step. Thus, the duration field 517 provides a drop down menu 517a listing a variety of duration units, as shown in FIG. 5F. The menu 517a may include, for example, "open" (indicating that no duration has been selected) "time," and "distance." Of course, other embodiments of the invention may provide still other units for determining a duration of an activity. Using this menu 517a (or, with some embodiments of the invention, entering a value directly into the duration field 517), the user selects a duration of the activity in step 607.

Figure 5G:
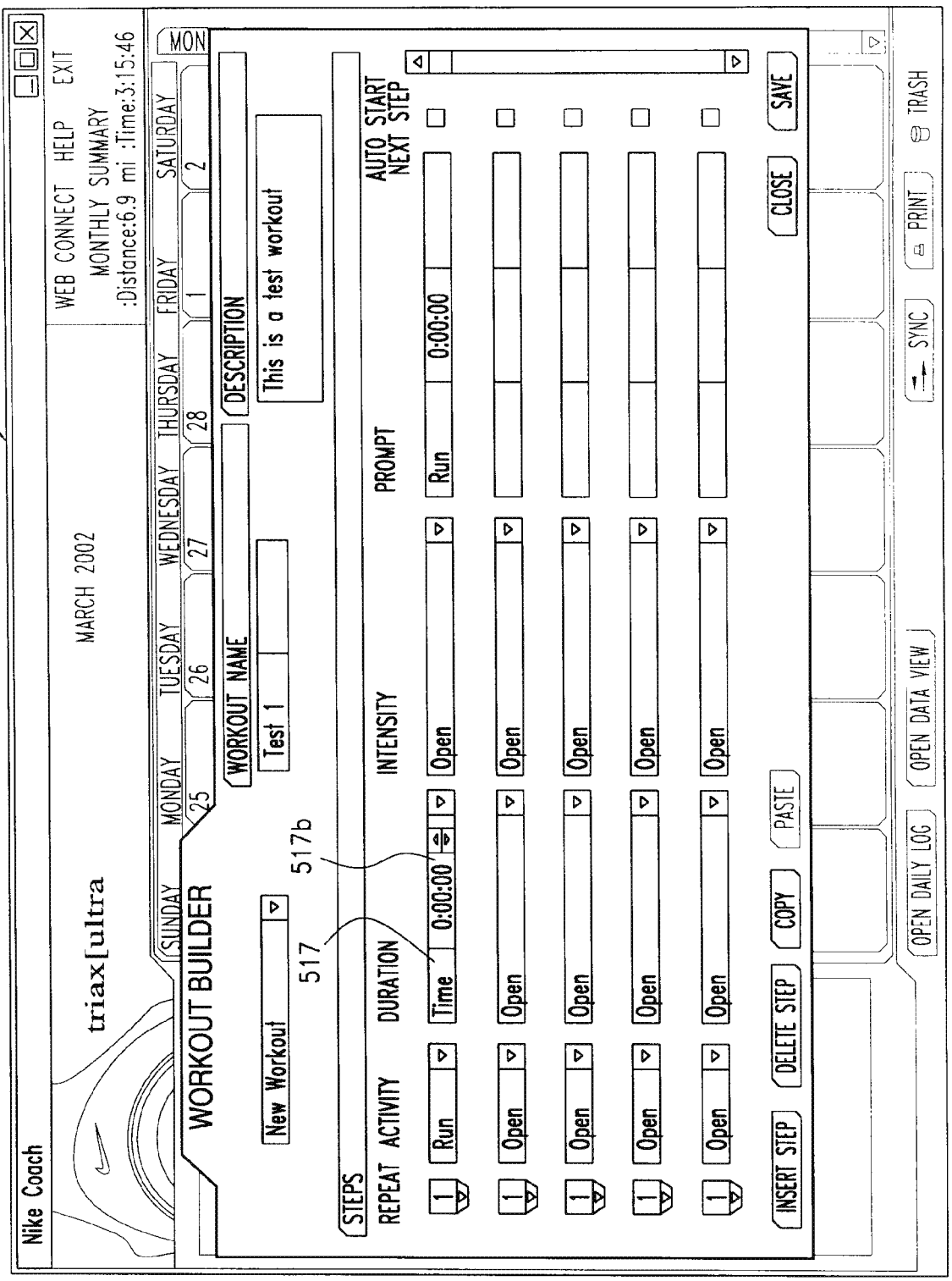

Depending upon the duration type selected for the duration field 517, the interface 501 may provide a sub-field corresponding to the selected duration type. For example, if the user selects the value "time" for the duration field 517, the interface 501 provides a time sub-interface 517b as shown in FIG. 5G. The time sub-interface 517b includes a chronographic display defining the time period for which the activity defined for the step is to be performed. Using conventional arrow buttons, the user can adjust the value of the sub-interface 517b to define a desired time period.

Figure 5H:
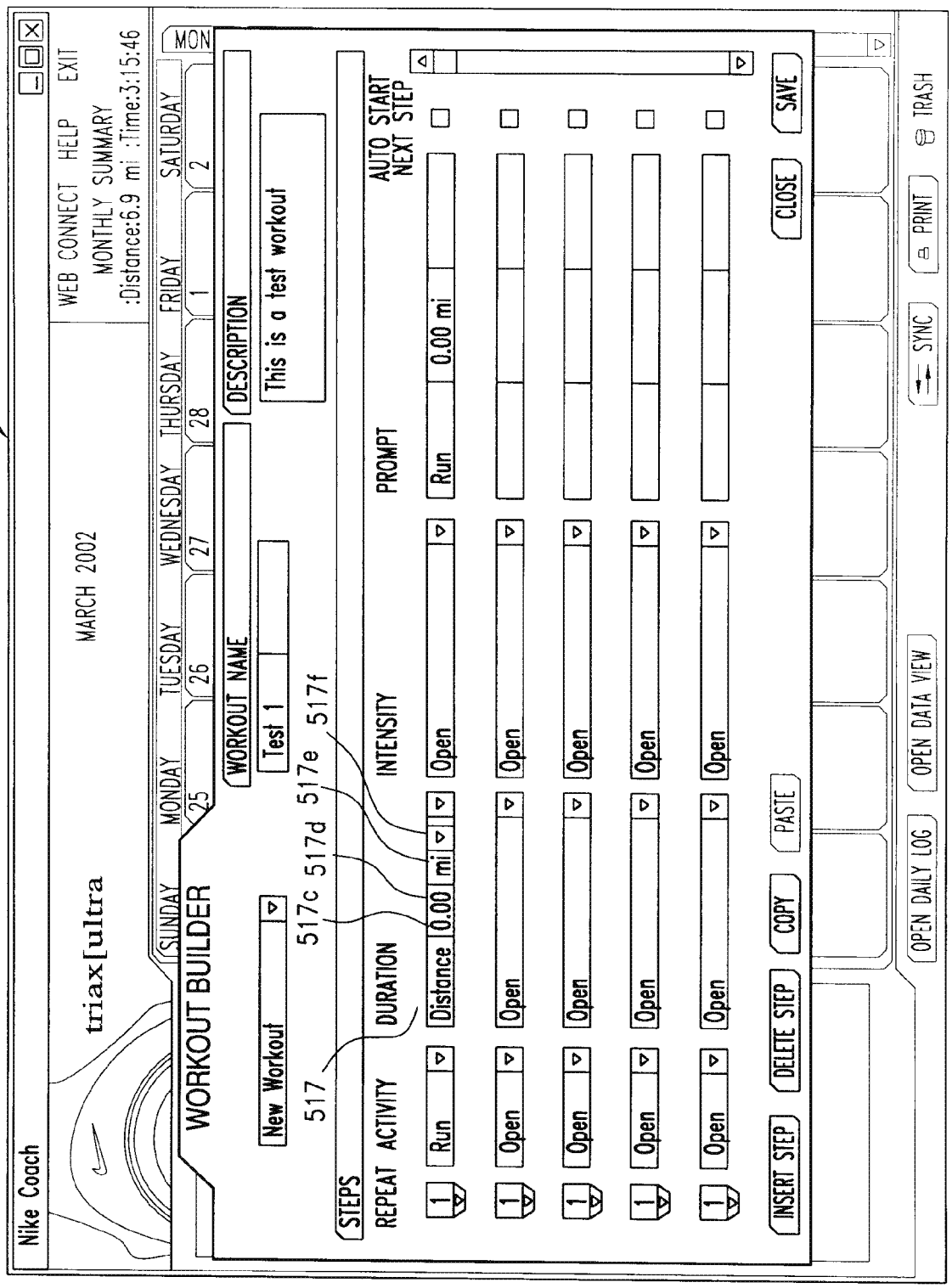

Similarly, if the user selects the value "distance" for the duration field 517, the interface 501 provides sub-interfaces 517c with fields 517d and 517e, as shown in FIG. 5H. The field 517d contains a value for a distance to be traveled while performing the activity. The user can type a desired value into this field 517d. The field 517e then provides a drop down menu, accessed by activating the button 517f, listing different distance units. For example, with the illustrated embodiment, the list includes "miles," "kilometers," and "meters." Of course, those of ordinary skill in the art will appreciate that still other distance units, such as "yards" and "feet," may be alternately or additionally included in the list.

Figure 5I:
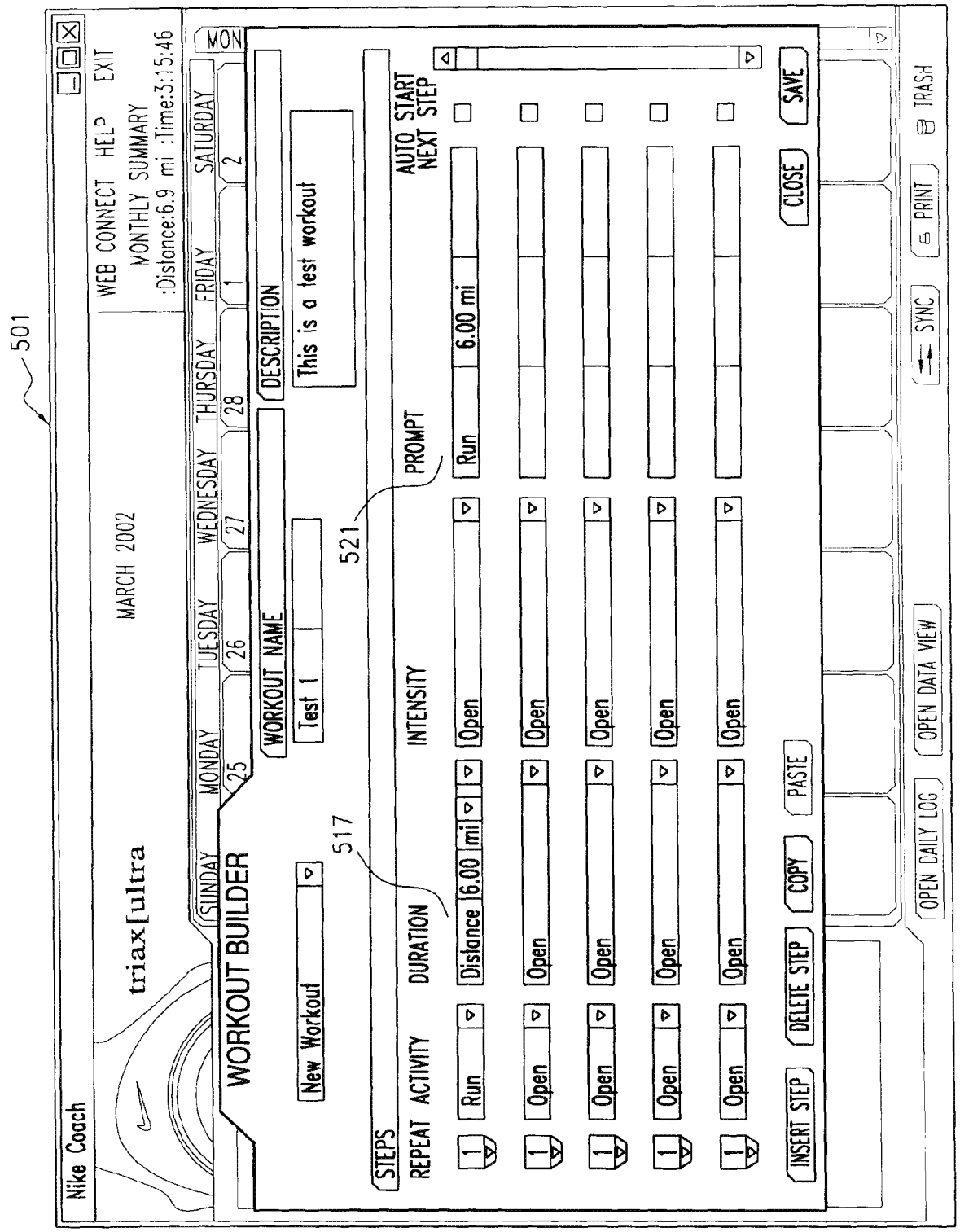

Thus, a user selects a particular type of duration, and enters values into the sub-interface fields associated with that type of duration in step 605. The values entered by the user then also appear in the prompt field 521. For example, if the user selects a duration value of "6.00 miles" for the duration field 517, this value also appears in the prompt field 521 as shown in FIG. 5I. It should be noted, however, that a user might choose not to select any values for a duration of the designated activity, and instead leave the value of the field 517 as "open." In this situation, no information is added to the prompt field 521, as shown in FIG. 5E.

Figure 5J:
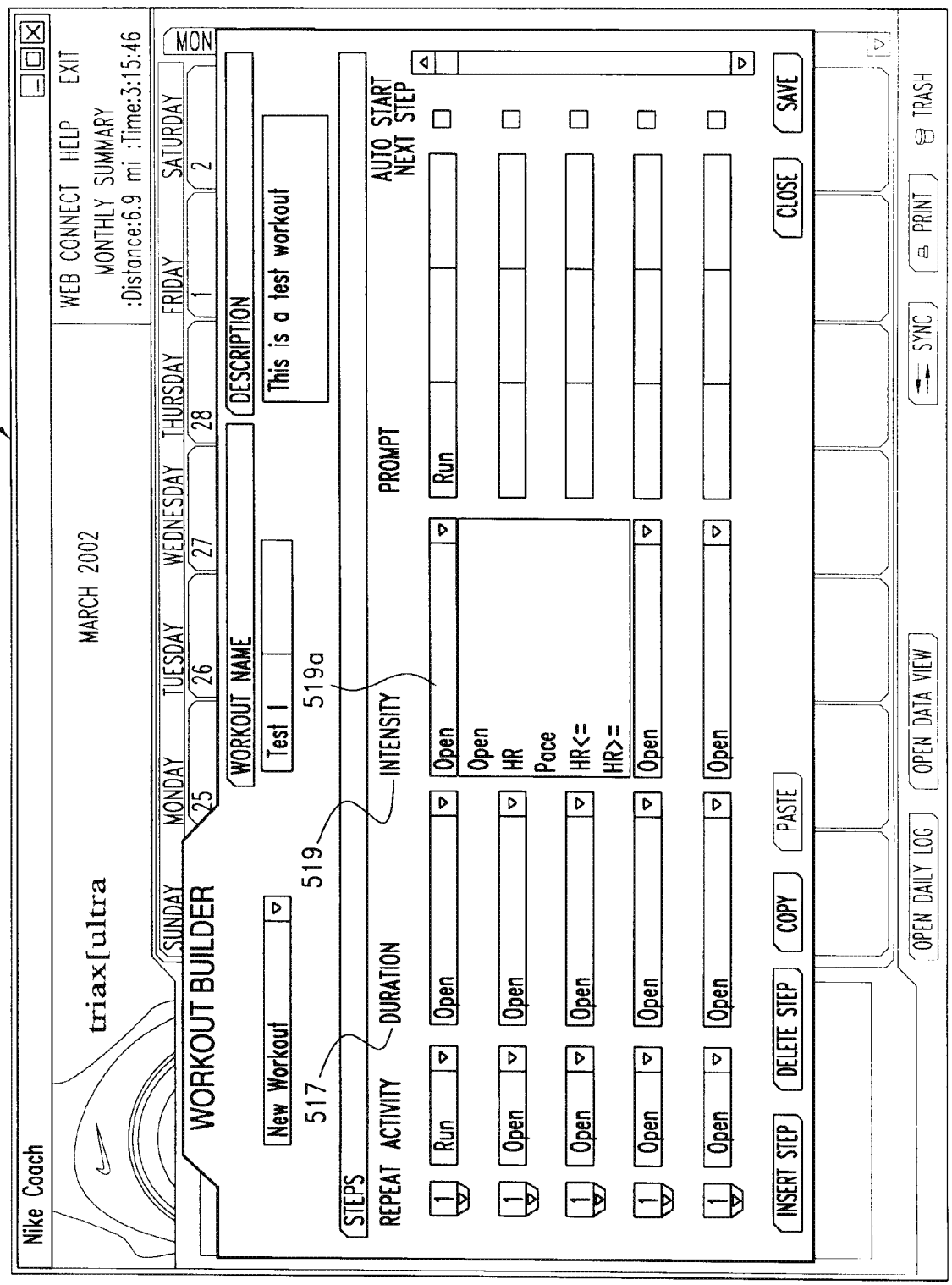

Next, in step 607, the user may select an intensity for the workout by entering a value into the intensity field 519. As seen in FIG. 5J, the intensity field 519 provides a drop down menu 519a listing different types of intensity measurements. For example, with the illustrated embodiment, the intensity field 519 provides a drop down list 519a including the intensity types "open" (when no value is selected), "heartrate," "pace", "heartrate less than or equal to," and "heartrate greater than or equal to." Of course, those of ordinary skill in the art will appreciate that other units of intensity may alternately or additionally be displayed. As with the duration field 517, when any of the units are selected from the drop down list 519a, the interface 501 provides a sub-interface associated with that type of intensity measurement.

Figure 5K:
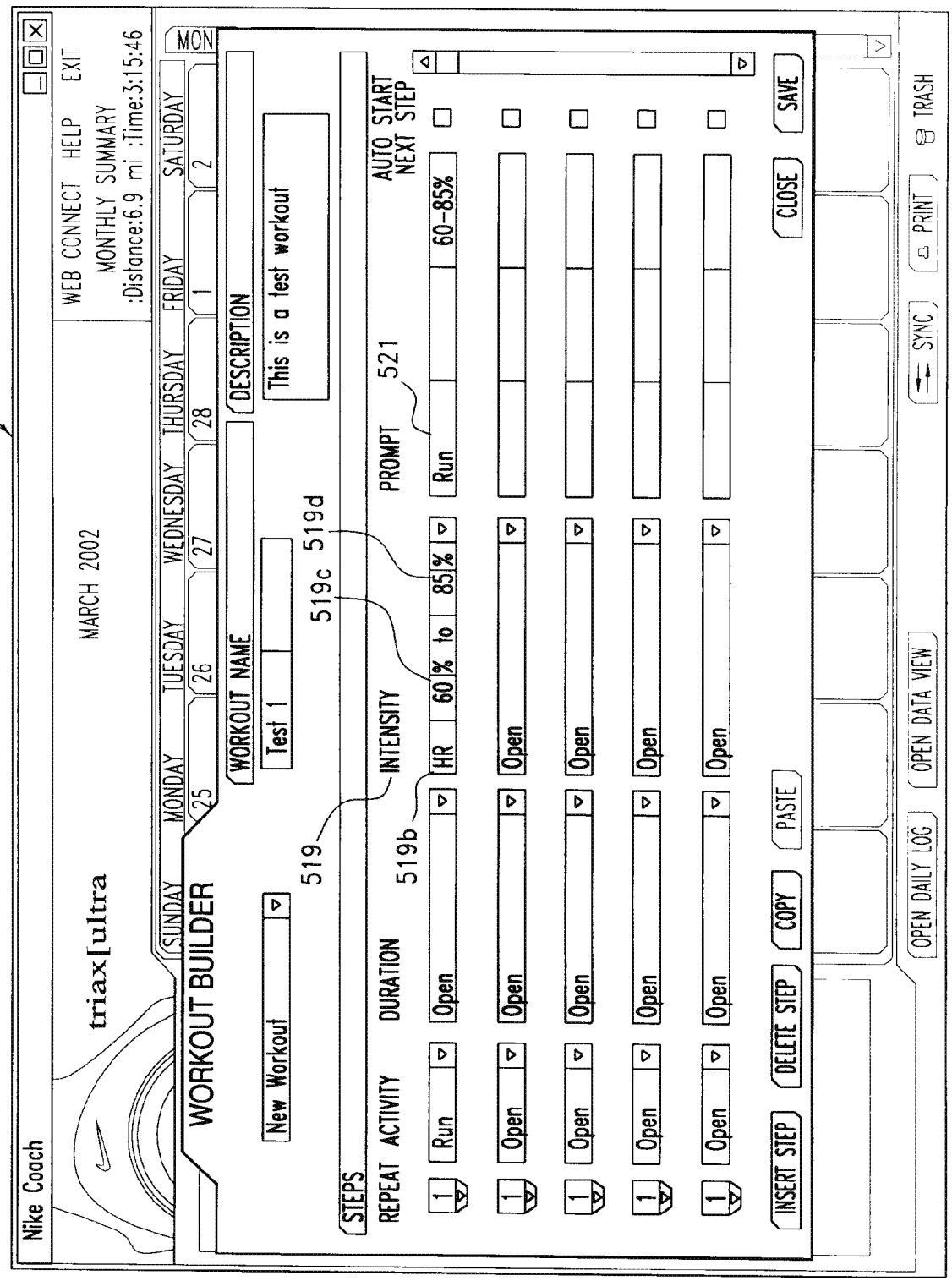

For example, if a user selects the intensity type "heartrate," the interface 501 provides the sub-interface 519b containing the fields 519c and 519d for defining a range of heartrates (measured based upon a percentage of a user's previously recorded maximum heartrate, for example), as shown in FIG. 5K. Thus, a user types a minimum desired heartrate percentage value into the field 519c and a maximum desired heartrate percentage value into the field 519d. The values entered into these fields are then displayed in the prompt field 521. For example, if the user enters the value 60% into the field 519c, and the value 85% in the field 519d, these values appear in the prompt field 521, as shown in FIG. 5K.

Figure 5L:
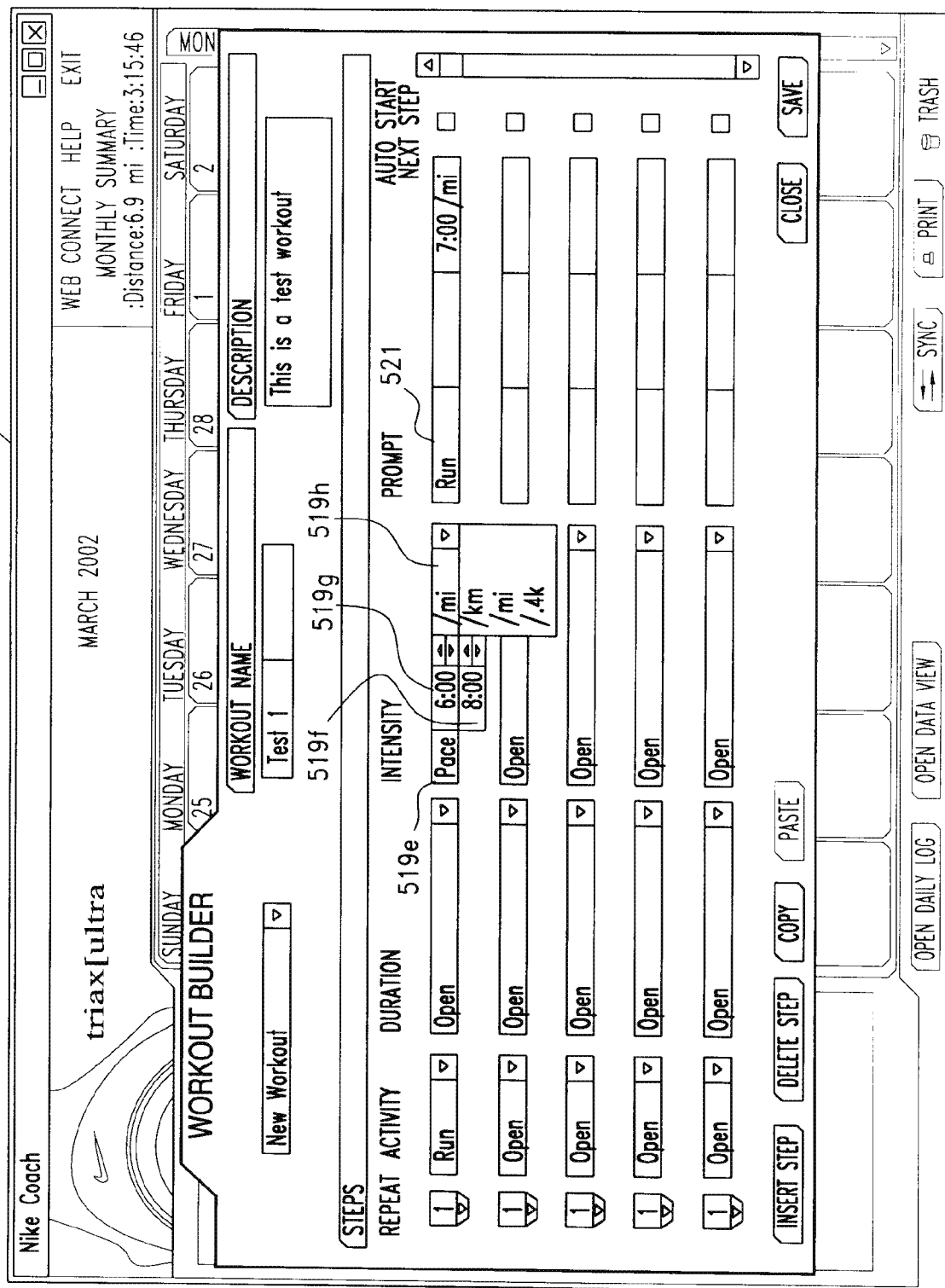

Similarly, if a user selects the intensity type "pace," the interface 501 provides the sub-interface 519e, as shown in FIG. 5L. The sub-interface 519e includes a maximum time field 519f and a minimum time field 519g, in which the user enters values to select a maximum pace time and a minimum pace time, respectively. The sub-interface 519e also includes a distance unit field 519h, which provides a drop down menu listing various distance units. With the illustrated embodiment, the menu lists "kilometers," "miles," and "0.4/kilometers." Of course, those of ordinary skill in the art will appreciate that the menu may include more, fewer, or different units. By selecting a maximum pace time, a minimum pace time, and a distance unit, the user can define a maximum and minimum pace for performing the selected activity. It should be noted that, as the values are entered into each of the fields 519f-519h, a mean of maximum pace time and the minimum pace time are added to the prompt field 521. Thus, if the user selects a maximum pace of 6:00 minutes per mile, and a minimum pace of 8:00 minutes per mile, the average of 7:00 minutes per mile will appear in the prompt field 521, as shown in FIG. 5L.

Figure 5M:
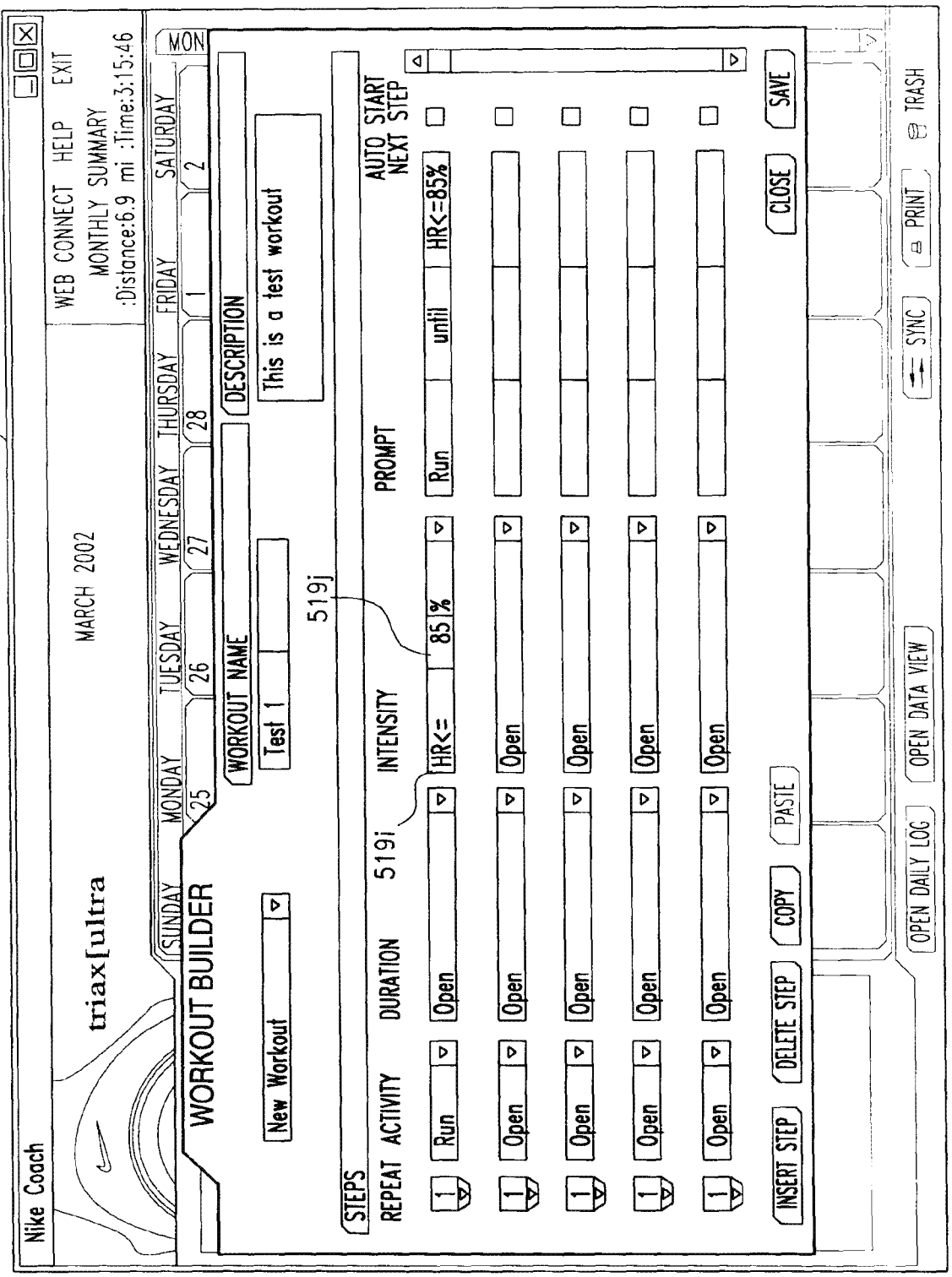
Figure 5N:
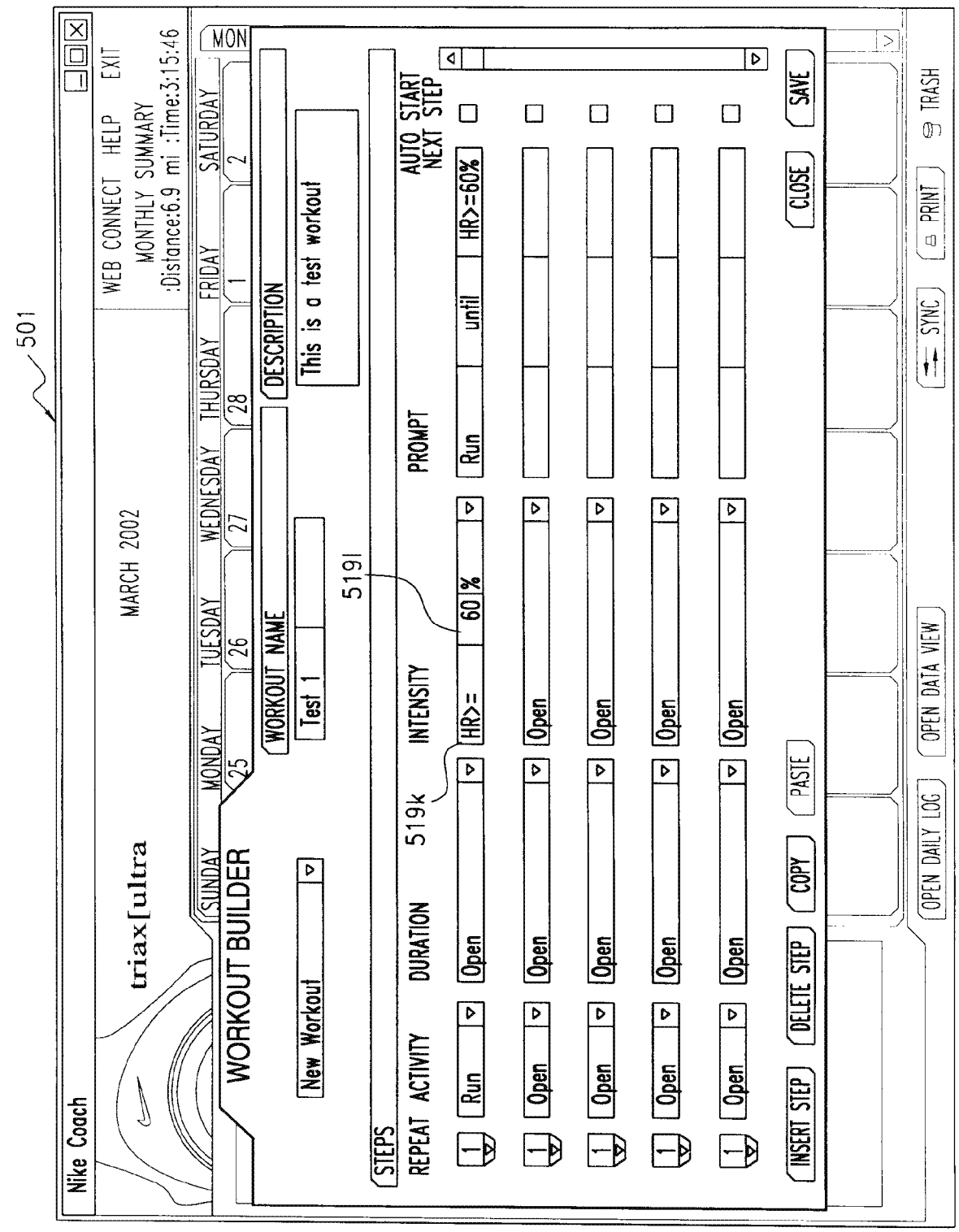
Figure 50:
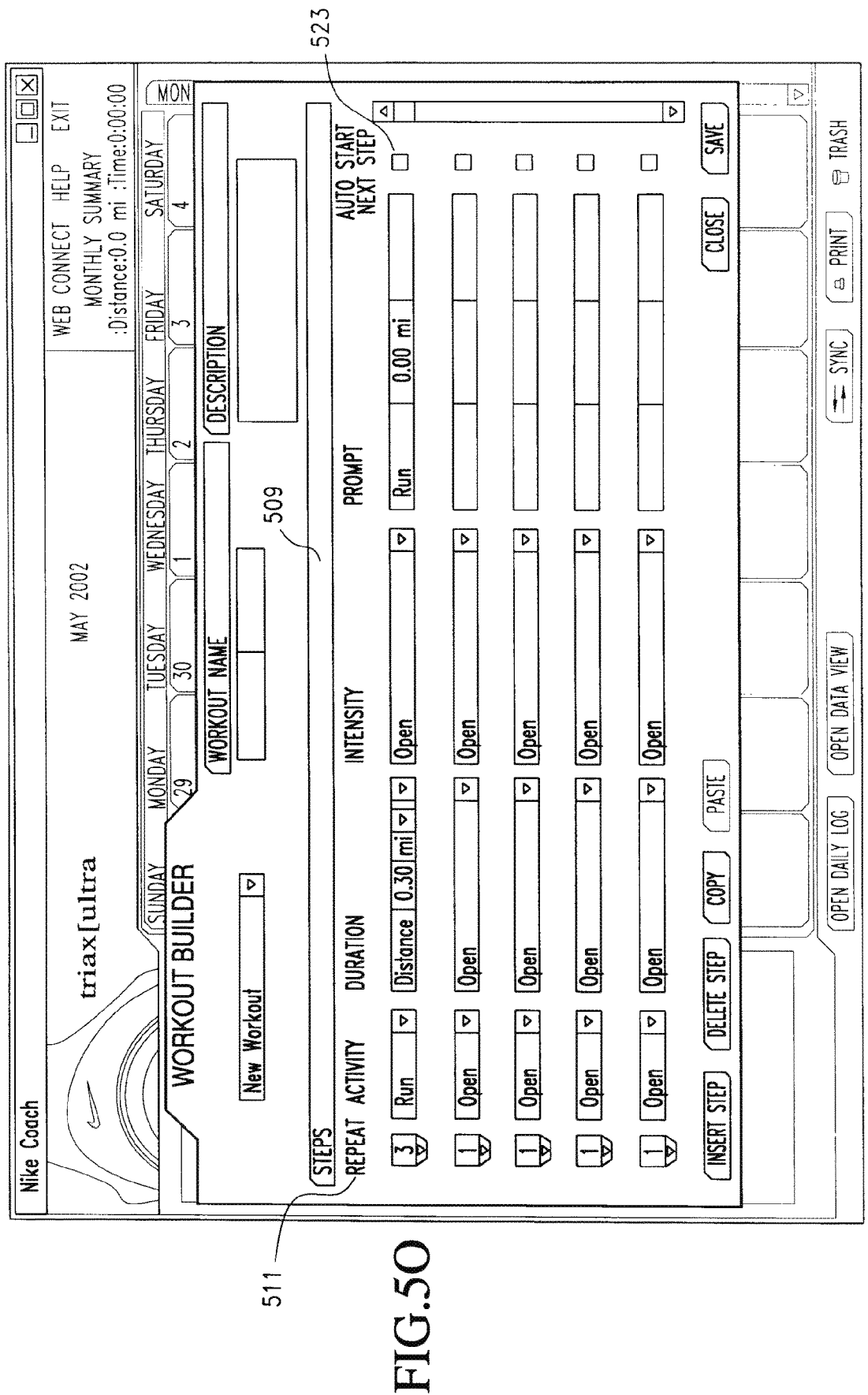

If the user selects the "heartrate less than or equal to" intensity type, the interface 501 provides the sub-interface 519i containing the field 519j, as shown in FIG. 5M. The user can simply enter a desired maximum heartrate (measured based upon a percentage of a user's maximum heartrate) into the field 519j. Likewise, if the user selects the "heartrate greater than or equal to" intensity type, the interface 501 provides the sub-interface 519k containing the field 519l, as shown in FIG. 5N. Again, the user can simply enter a desired minimum heartrate (measured based upon a percentage of a user's maximum heartrate, for example) into the field 519k. With both sub-interfaces 519i and 519k, the selected heartrate value is then displayed in the prompt field 521.

In this manner, a user will employ fields 515-519 of a step sub-interface 511 to define one step of a training script. By entering values into the fields of multiple step sub-interfaces 511, a user may create a training script with a plurality of steps sequentially arranged in the order displayed in the step listing 509. When the training script file is then created from the training script, it will contain instructions commanding the servant device 211 to sequentially display the value of the prompt field 521 (that is, the prompt) for each step, starting with the first step in the sequence, until the servant device 211 is instructed to display the value of the prompt field 521 for the next step.

The servant device 211 may receive an instruction to display the prompt for the next step of the training script file directly from the user. For example, if the servant device 211 is implemented as a digital watch, it may display the prompt for a step until the athlete using the servant device 211 depresses a command button, and then start the next sequential step in the training script file by displaying the prompt for that next sequential step. Thus, a user would perform the activity displayed in the prompt for a step for the duration and/or intensity specified in the prompt. Then, when the activity was completed, the user would depress the command button to start the next step. That is, the user would depress the command button to instruct the servant device 211 to display the prompt for the next step in sequence. Alternately, when a step is completed, the servant device 211 may receive an instruction to automatically start the next sequential step from within the instructions for the completed step, as will be explained below.

When creating or editing a training script, the user determines whether a step will have this automatic start feature by placing a check value in the auto start field 523 for that step's sub-interface 511 in step 609. More particularly, if the user leaves the auto start field 523 for a step empty in step 609, then the training script will not include an instruction in that step for the servant device 211 to automatically begin executing the instructions for the subsequent step. Instead, when that step is completed, the servant device 211 will temporarily stop executing instructions of the training script until receiving an input from the athlete using the servant device 211. On the other hand, if the user inserts a check into the field 523 of a step's sub-interface 211 in step 609, the resulting training script file will include instructions to automatically have the servant device 211 begin executing the instructions for the subsequent step when that step is completed.

As will be discussed in detail below, the servant device 211 may have one or more sensors 113d for measuring characteristics of the user's workout or performance data. These characteristics may include, for example, a time duration measured by a chronometer, a heart rate measured by a heart rate monitor, and a distance measured by an accelerometer or pedometer. These sensors 113d allow the servant device 211 to detect when a user has completed a specified duration or intensity for a step. For example, if the user selects the duration of a step to be six minutes, then a servant device 211 having a chronometer may begin measuring a period of six minutes from when the step is started (that is, from when the value of the field 521 for that step is displayed to the user). If the value of the field 523 for that step was checked when the training script was created, then the training script file will include instructions commanding the servant device 211 to automatically begin executing the instructions for the subsequent step when the chronometer indicates that the six minute time period has expired.

Similarly, a step may call for a user to run a distance of six miles at a heart rate of 60% of the user's maximum heart rate or greater. If a servant device 211 executing that step had both a pedometer and a heart rate monitor, it could employ the pedometer to measure the distance run by a user and the heart rate monitor to measure the user's heart rate during that run. The servant device 211 could then record a total distance traveled by the athlete while the athlete's heart rate was above the minimum amount. If the user had placed a check in the auto start field 523 when defining the step, then the instructions in the training script file would command the servant device 211 to automatically begin executing the instructions for the next subsequent step after the servant device 211 detected that the athlete had run a total of six miles with his or her heart rate above the minimum amount.

Thus, by using creating a training script with steps that automatically start a subsequent step when the defined performance data is measured, the invention advantageously frees an athlete from having to constantly consider the status of his or her workout routine. That is, an athlete can focus on each activity of a workout, without having to continuously monitor if the athlete is complying with the planned duration or intensity for the activity. The servant device 211 informs the user when an activity has been satisfactorily performed by prompting the athlete to begin performing the next scheduled activity in the workout.

Figure 5P:
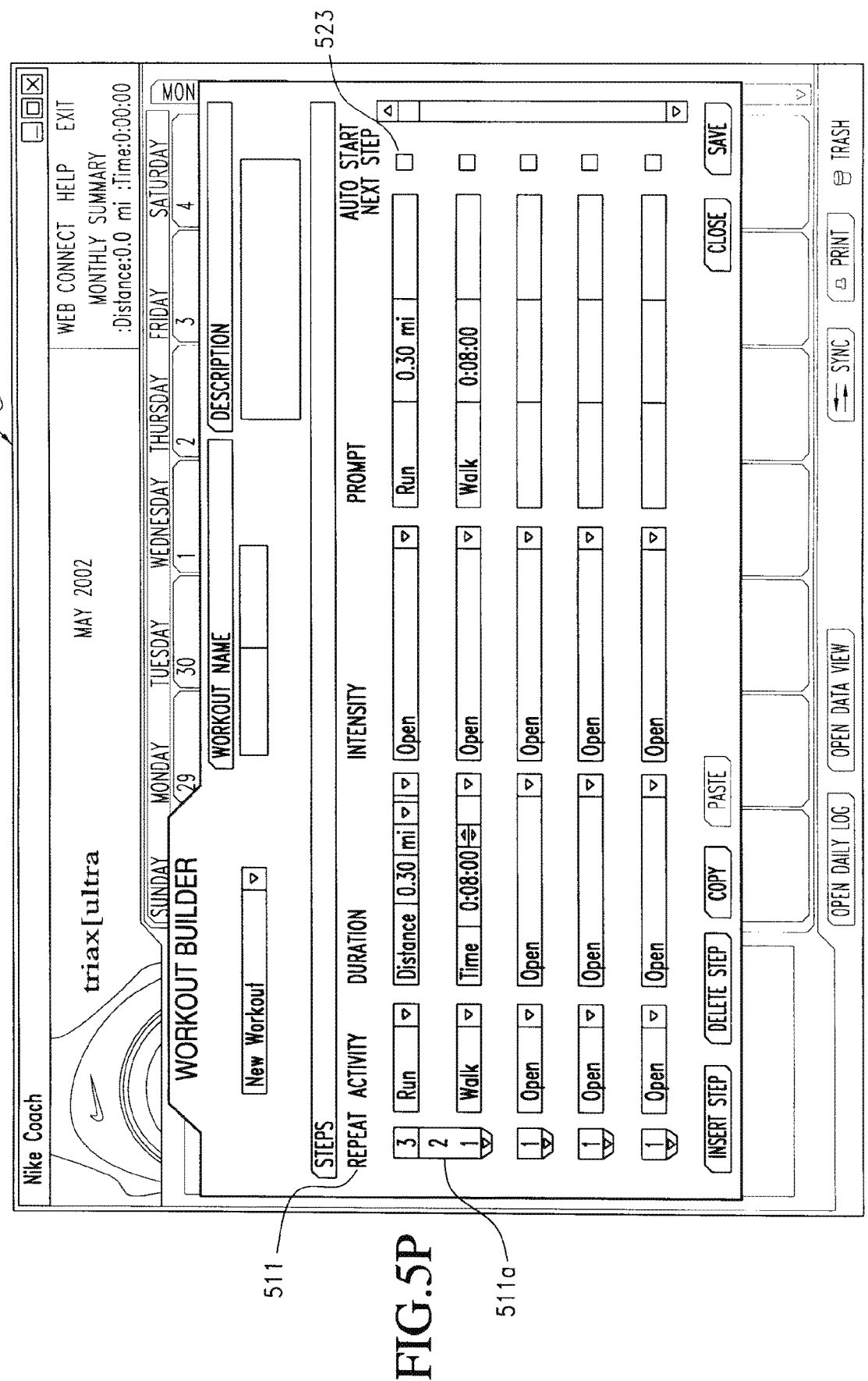

In addition to the auto start field 523, each step sub-interface 511 also includes a repeat field 511, as noted above. In step 611, a user may employ the repeat field 511 to define a training script that repeats one or more steps. For example, if the user inputs the value "3" into the repeat field 511 for a step, as shown in FIG. 5O, then the training script file will include instructions commanding the servant device 211 to repeat the step three times before executing the next sequential step. In addition, the user may use a linking arrow 511a attached to the repeat field 511 to link two or more sequential steps together for repetition, as shown in FIG. 5P. Thus, the resulting training script would include instructions commanding the servant device 211 to execute the instructions of the first three steps listed in the step listing 509 once in sequence, and then to repeat the execution of these linked steps a second time before proceeding to the fourth step in the step listing 509 (that is, the "jog" step).

After the user has created a training script file by saving the steps making up a desired training script in step 613, the user may return to the interface 401 shown in FIG. 4A. Advantageously, in addition to allowing a user to create a new training script file or modify an existing training script file, the master device 201 will also allow a user to define a schedule of training scripts, hereafter referred to as a "plan." The creation of a plan will be discussed with reference to FIGS. 7A-7C and FIG. 8, which illustrate an interface 701 for creating a plan and a flow chart for using the interface 701 to create a plan, respectively.

As previously noted, the plan field 405 of interface 401 displays existing plans. If the user wishes to create a new plan, the user activates the plan builder command button 407a. In response, the master device 201 provides the user interface 701 illustrated in FIG. 7A. This user interface 701 includes a plan selection field 703, a plan name field 705, and a plan description field 707. In step 801, the user enters the name of the desired plan into the plan selection field 703. Conveniently, the plan selection field 703 may include a drop-down menu 703a, as shown in FIG. 7B. If the user is editing an existing plan, the user may simply select the name of that plan from the drop-down menu 703a. If, however, the user wishes to create a new plan, the user selects the name "New Plan" from the drop-down menu 703a. The user may then enter a name into the planned name field 705 and a brief description of the new plan in field 707, as also shown in FIG. 7B.

The interface 701 also includes a settings sub-interface 709, a workout sub-interface 711, and a calendar sub-interface 713. The calendar sub-interface displays a generic calendar with columns corresponding to the days of the week, while the workout sub-interface 711 displays a listing of existing training script files. In order to create or modify a plan, in step 803 a user drags each training script file from the workout sub-interface 711 to the desired location on the calendar sub-interface 713.

Figure 7A:
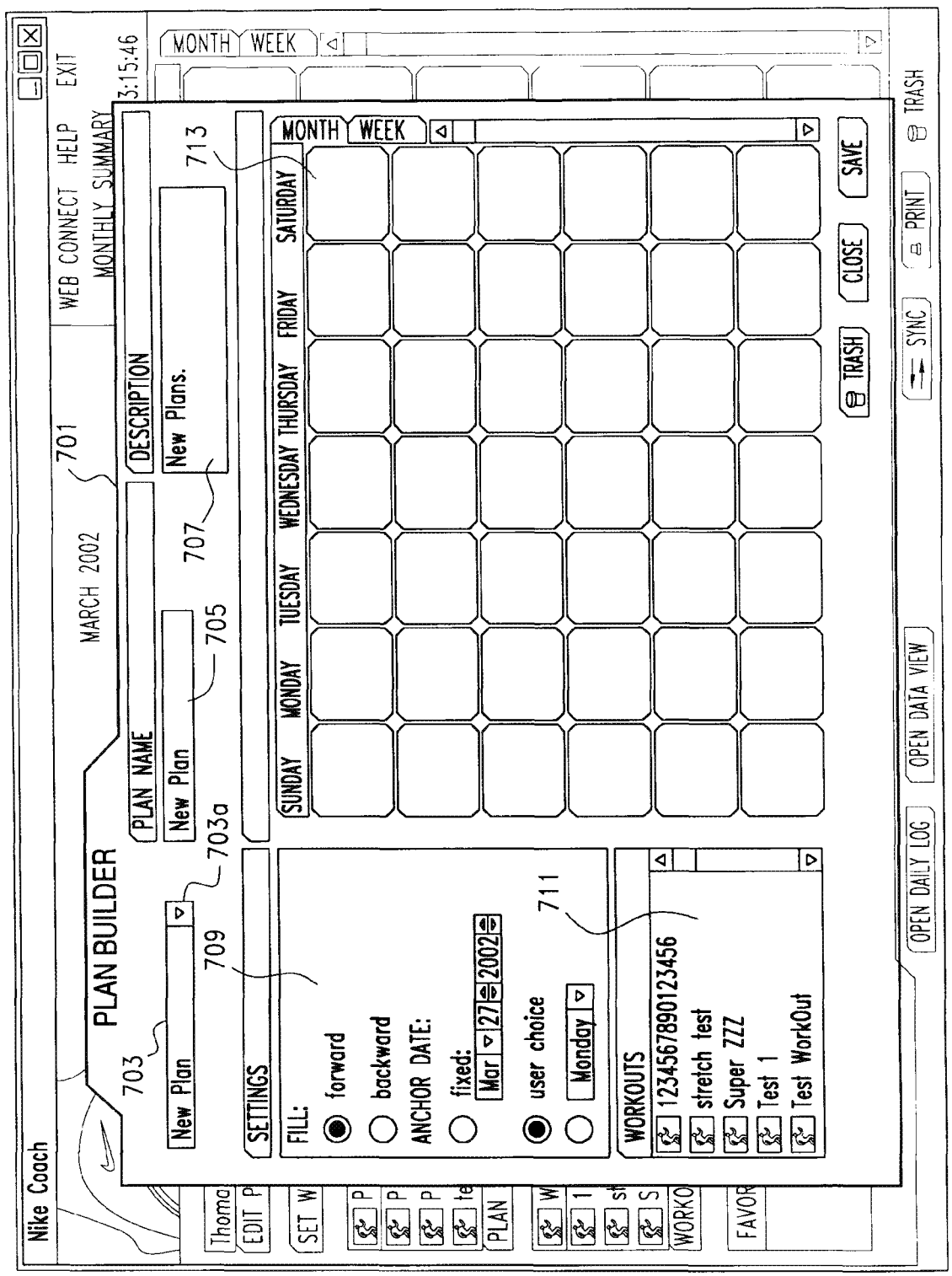
Figure 7B:
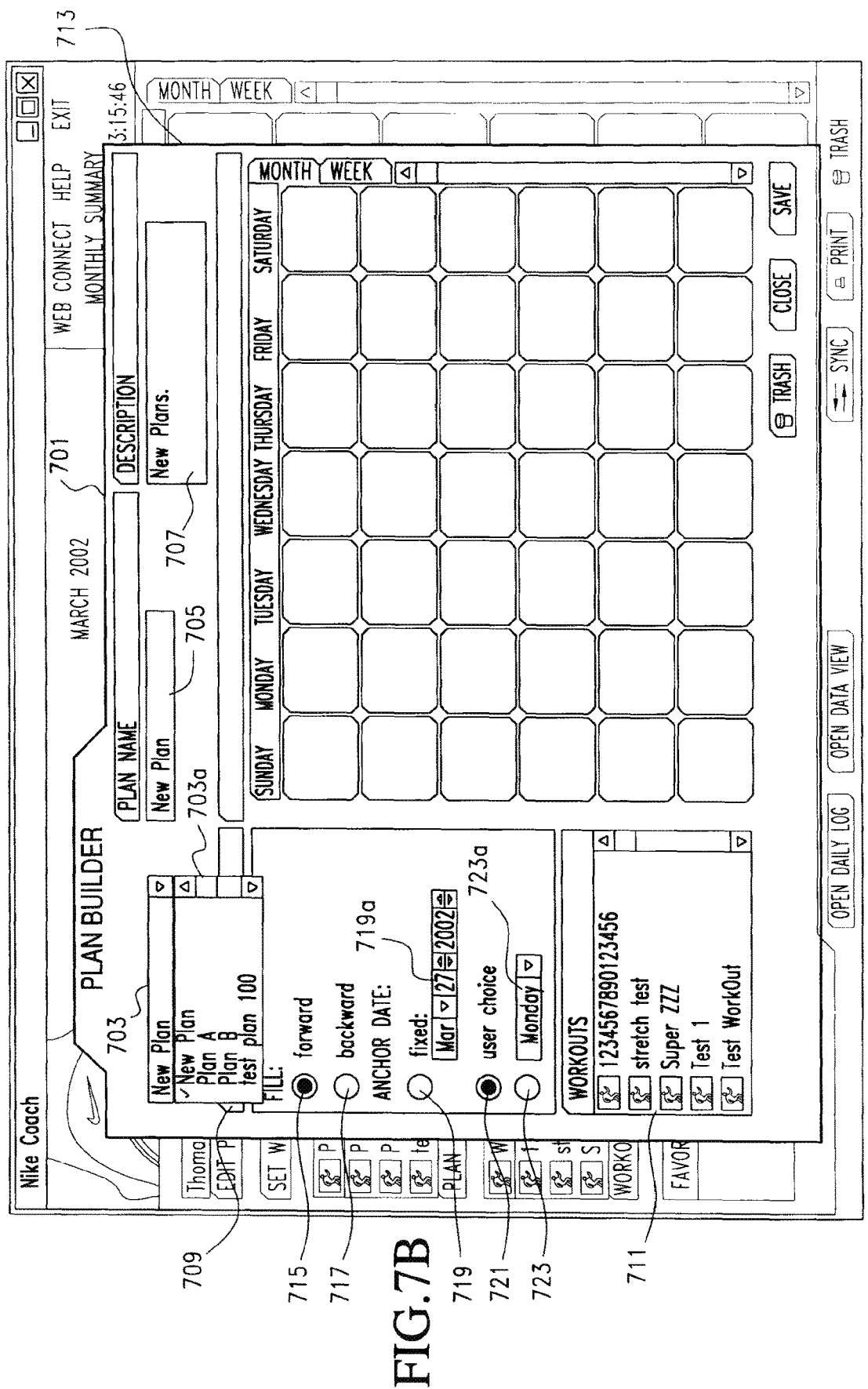
Figure 7C:
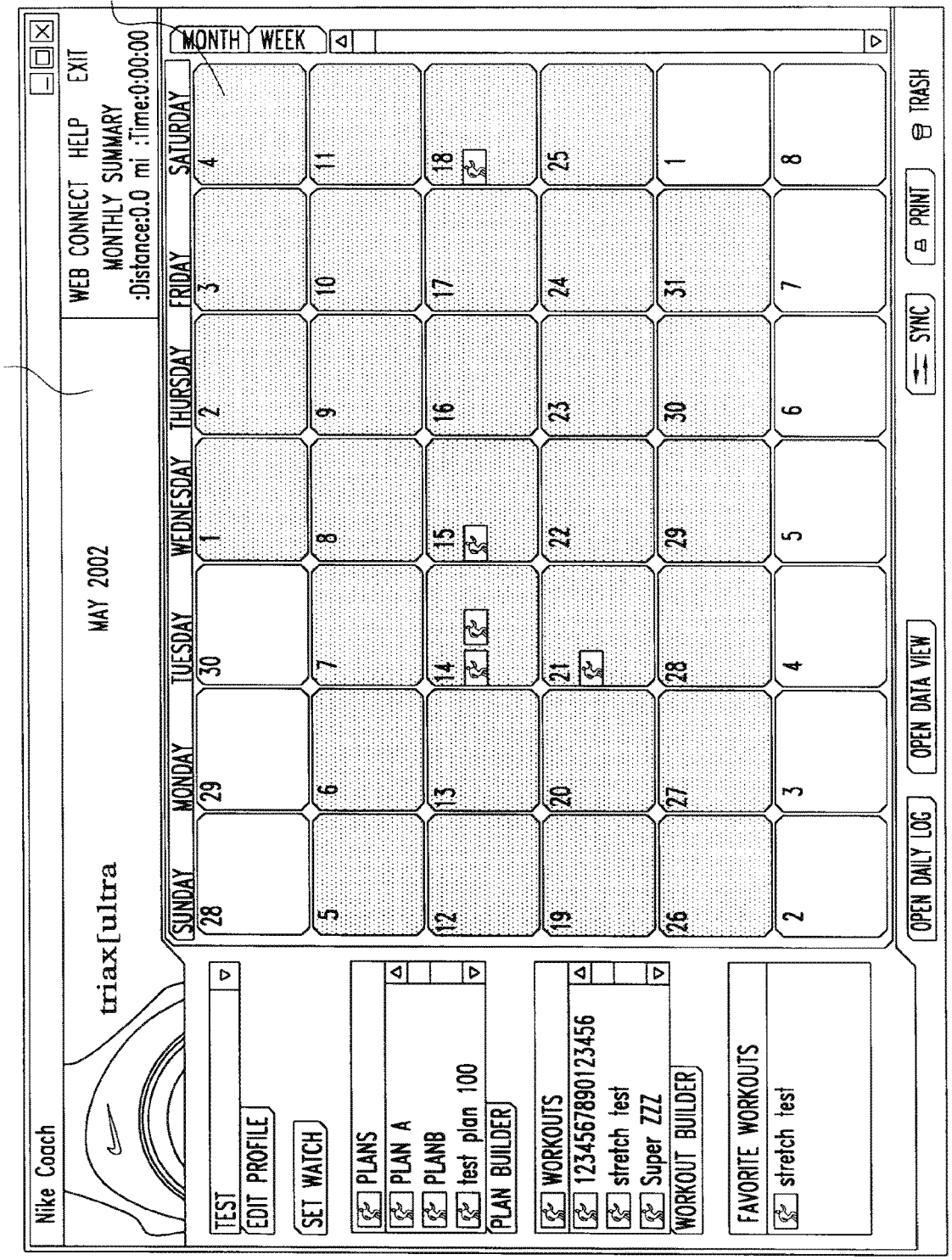
Figure 8:
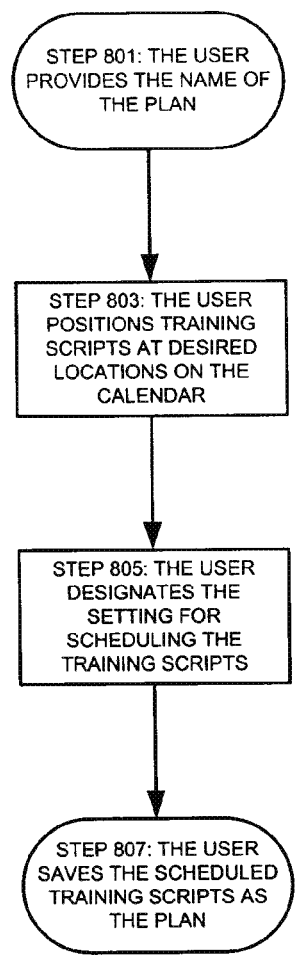
FIG. 8 illustrates a flow chart for using an interface according to an embodiment of the invention to create a plan of one or more training scripts.

For example, in FIG. 7A, the workout sub-interface 711 lists the training script files entitled "stretch test," "Test 1," and "Test workout." The user may want to create a three-week workout plan having the "stretch test" workout scheduled on the Monday, Wednesday, and Friday of the first week of the plan. The user may also want the "Test 1" workout scheduled on the Sunday, Tuesday and Thursday of the second week of the plan, and the "Test workout" workout scheduled on the Monday and Thursday of the third week of the plan. To create this plan, the user can simply drag and drop icons for the corresponding training script files to the desired locations on the calendar sub-interface 713, as shown in FIG. 7C.

The module of dragging and dropping file icons is well known, and thus will not be discussed here in detail. Of course, those of ordinary skill in the art will appreciate that alternate techniques may be used to schedule training script files. Also, as seen in FIG. 7C, the calendar sub-interface 713 may not continuously display the titles of the placed training script file icons, but may instead only display their titles when, for example, the user places a pointer over an icon. Alternately, the calendar sub-interface 713 may display the title of each icon placed in the calendar sub-interface 713.

Once the user has placed the desired training script files at the appropriate locations in the calendar sub-interface 713, the user designates the settings for scheduling the training script files to create or edit the plan in step 805. As previously noted, the interface 701 includes a settings sub-interface 709. The settings sub-interface 709 includes two fill radial buttons 715 and 717, entitled "forward" and "backward," respectively. It also includes three anchor date radial buttons 719-723. Beneath the first anchor date radial button 719, entitled "fixed," is a calendar field 719a that allows a user to select a specific month, date and year. The second anchor date radial button 721 is entitled "user choice." The third anchor date radial button 723 includes a drop-down menu 723a listing the days of the week.

In order to establish a workout plan, the user anchors the first date or the last date of the training script files scheduled in the generic calendar of the calendar sub-interface to an actual date. For example, the user may with to schedule training script files to prepare for a marathon on Nov. 13, 2002. Accordingly, the user may want to anchor the plan so that the last workout of the plan takes place on Nov. 12, 2002. To do so, the user would select the anchor date radial button 719, and set the value of the calendar field 719a to Nov. 12, 2002. The user would then select the "backward" fill radial button 717, to have the plan scheduled backward from the last workout of the plan occurring on Nov. 12, 2002.

Alternately, the user may want to schedule a three-week plan that starts on the first Tuesday of each three-week period. In this case, the user would select the anchor date radial button 723, and select the day Tuesday from the drop down menu 723a. The user would also select the "forward" fill radial button 715, to have the plan scheduled forward from the first workout of the plan occurring on the first Tuesday of each three-week period.

Accordingly, in step 803, the user selects a fill setting for the plan, and in step 805 selects an anchor date for the plan. Then in step 807, the user activates the "save" button 725 to save the plan, completing the plan creation process.

Figure 4B:
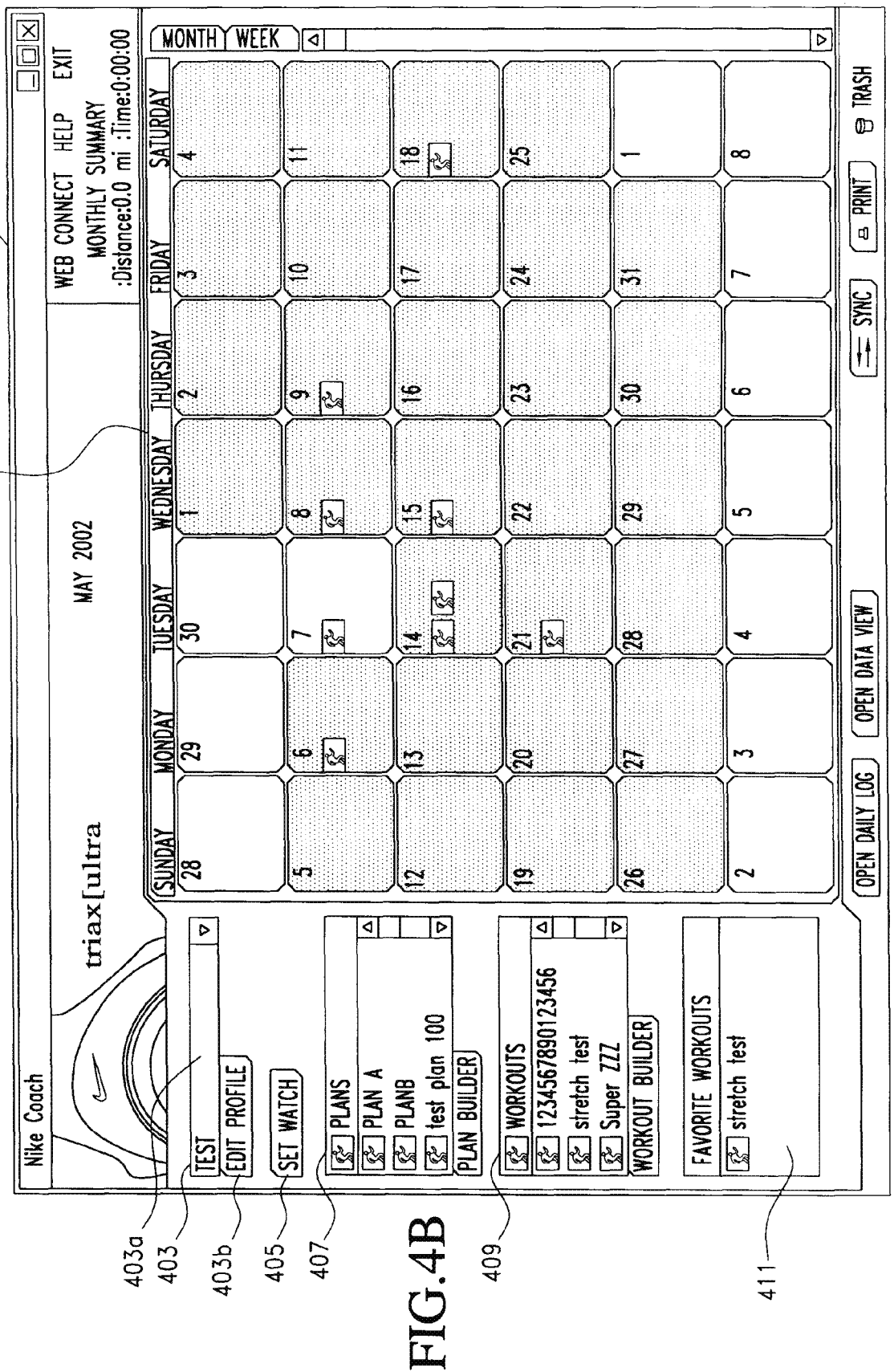
Figure 9:
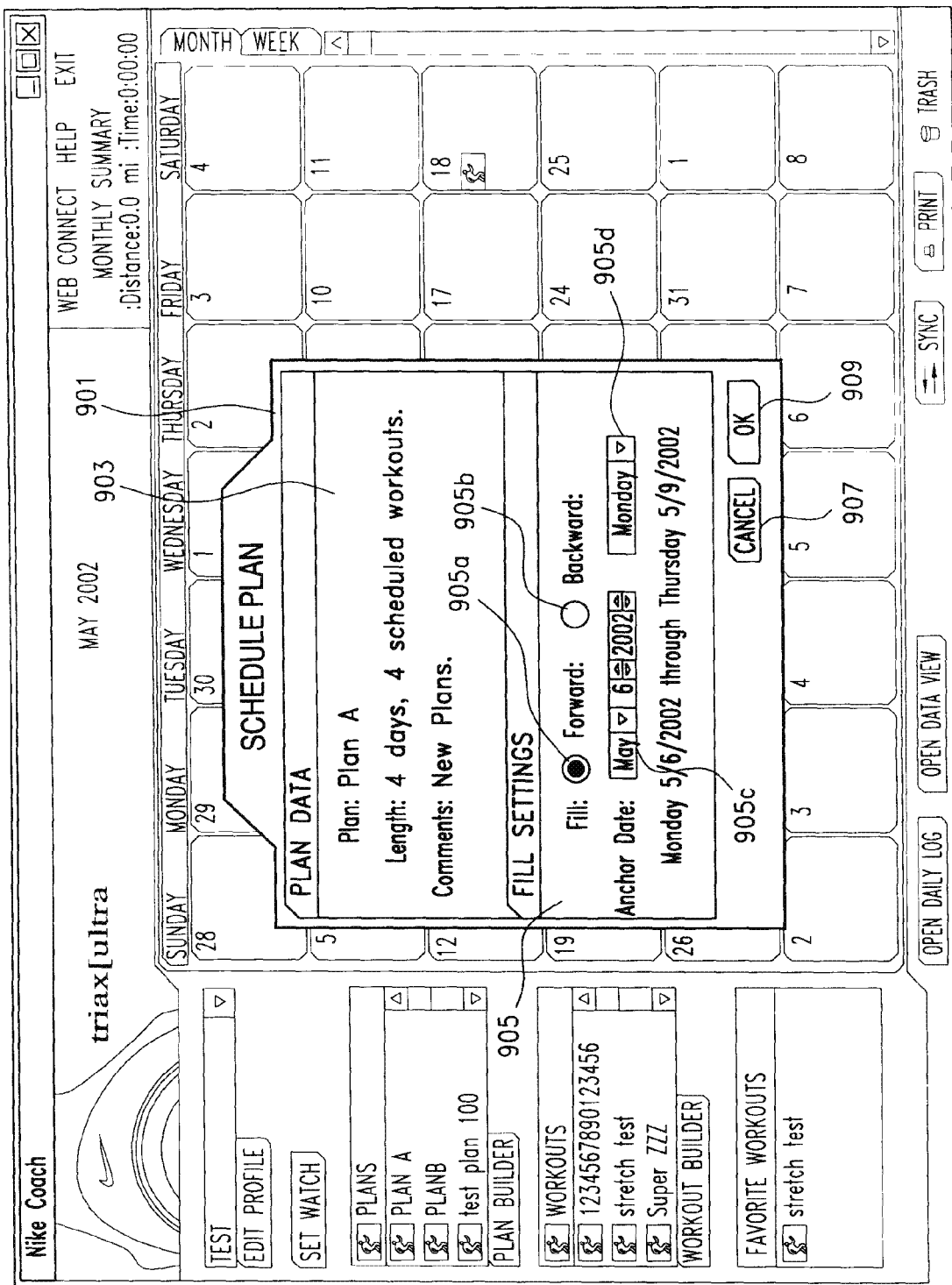

Returning now to FIG. 4A, a user may select a schedule for plans or individual training script files to be included in the user's profile. As previously noted, the interface 401 includes a calendar sub-interface 413. The calendar sub-interface 413 displays a calendar showing the current month. To include a plan in the user's profile, the user first drags and drops a plan onto a date in the calendar sub-interface 413, as shown in FIG. 4B. In response, the master device 201 displays the schedule plan interface 901 shown in FIG. 9.

As seen in this figure, the plan interface 901 includes a plan data sub-interface 903, a fill setting sub-interface 905, a "cancel" button 907 and an "ok" button 909. The plan data sub-interface 903 includes the plan name, the length of the plan schedule, and the description of the plan. The fill setting sub-interface 905 includes two fill dial buttons 905a and 905b, entitled "forward" and "backward," respectively. The fill setting sub-interface 905 also includes an anchor date field 905c, which allows the user to specify a specific calendar date, and a drop down menu 905d listing the days of the week. As with the settings sub-interface 709 in the interface 701, the user may employ the fill setting sub-interface 905 to anchor the plan. When the user is satisfied that the plan schedule is correct, the user activates the "ok" button 909. In response, the master device 201 may place icons for the training script files making up the plan on their appropriate dates in the calendar sub-interface 413.

As previously noted, in addition to placing a plan schedule in the user profile, a user may also place a schedule for individual training scripts into the his or her user profile. That is, a user may drag and drop an icon for a single training script file from the workout sub-interface 409 at a desired location on the calendar sub-interface 413.

Synchronizing the Master Device with the Servant Device

When a user wishes to download training script files from the master device 201 to the servant device 211, referred to as "synchronizing" the master device 201 with the servant device 211, the user activates the "sync" button 415 in interface 401. In response, the master device 201 transfers all of the training script files listed in the favorite workouts sub-interface 411. In addition, the master device 201 transfers the upcoming scheduled training script files that have been place in the calendar sub-interface 413.

More particularly, the master device 201 notes the date of the synchronization, and identifies the subsequent dates for, for example, the upcoming week. The master device 201 then attaches a date tag to each of the training script files that have been placed in the calendar sub-interface 413 on the dates in the week following the synchronization date, and transfers these training script files with their associated date tags to the servant device 211. As will be discussed further below, the servant device 211 can then employ these date tags to ensure that the training script file is presented to a user for execution on the date scheduled with the master device 201.

In addition to transferring training script files to the servant device 211, the master device 201 may also receive information from the servant device 211 during synchronization. For example, with some embodiments of the invention, the servant device 211 may collect actual data regarding a user's workout, including the actual duration or intensity completed for activities listed in a training script file. The master device 201 can then associate this data with the icons for those training scripts in the calendar sub-interface 413. This conveniently allows a user to review his or her athletic performance in comparison with the criteria of the training script.

Device for Executing a Training Script

As previously noted, FIG. 1 also illustrates a servant device 211 for executing a training script. The servant device 211 includes a servant control module 213, a servant device interface module 215, and a servant script database 217. The servant device interface module 215 receives a training script file from the master device 201. The servant control module 213 then stores the training script file in the servant script database 217.

The servant device 211 also includes a display 219 and one or more sensors 221 (identified as sensors 115d in the above description of a general computer device) for detecting a characteristic of a user during a workout. The sensors 221 may include, for example, a heart rate monitor to measure a user's heart rate, an accelerometer, pedometer or Global Positioning Satellite (GPS) receiver to measure the distance that a user travels, or a blood pressure monitor to monitor a user's blood pressure. The sensors 221 may also include sensors for detecting a characteristic of the user's workout itself. For example, the sensors 221 may include a chronometer or chronograph for measuring time periods during which an action is performed. The sensors 221 may also include a bicycle force sensor, to measure an amount of force produced by a bicyclist while biking. Still further, the sensor 221 may be a special purpose sensor that can, for example, detect the operation of a weightlifting machine or other exercise device configured to provide performance data to the sensor. Of course, any suitable device for measuring performance data relating to a workout may be used as a sensor 221.

Still further, the servant device 211 may include a servant user interface module 223 for detecting an input by a user. For example, the servant device 211 may have a servant user interface module 223 for detecting the depression of an input button. This servant user interface module 223 allows a user to input data to the servant device 211 regarding the user's workout that may not easily be detectable by a sensor 211. For example, a training step may call for an athlete to perform 30 repetitions of a weight lifting exercise. An automated sensor cannot easily detect the number of repetitions of a weight lifting exercise using a convention weight lifting device. The athlete, however, may conveniently depress a command button after having performed the scripted 30 repetitions. The servant user interface module 223 can then detect the depression of the command button, and forward this information to the servant control module 213.

When an athlete wants to exercise according to a training script, the user selects the training script file with that training script from the servant script database 217. In response, the servant control module 213 executes the appropriate instructions defined in the training script. More particularly, by executing the instructions in the training script file, the servant control module 213 causes the display 219 to display the prompt for each step included in the training script file. As previously noted, the display 219 will sequentially display the prompt for each step in the training script until the servant control module 213 receives an instruction commanding the display 219 to display the prompt for the next step. As was also previously explained, this instruction may be provided directly from the user by, for example, the user depressing a command button. Alternately, this instruction may be automatically generated when one of the sensors 221 measures a specified value, as discussed in detail above.

CONCLUSION

Thus, the master training script device of the invention conveniently allows a user to create a training script defining one or more steps of a workout routine, where each step may include an activity, a duration for performing that activity, and an intensity at which the activity is to be performed. Further, one or more steps of the training script can be self starting in response to performance data detected by sensors of the servant training script device. This conveniently frees the athlete from having to continuously monitor the status of his or her workout activities. Still further, the training script device conveniently allows a user to transfer training scripts to other training script devices, so that athletes can share successful training scripts.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A device for creating a training script for a workout, comprising
    a user interface module that prompts a user to input data specifying a step in a training script;
    a control module that creates training steps to operate a user computing device to display a prompt for the training steps and to compile the training steps into the training script;
    a script database that receives and stores the training script; and
    a device interface module that synchronizes one or more training scripts in the script database with the user computing device, wherein the user interface module allows the user to define a user profile, the user profile having a group of training scripts relating to favorite workouts, and wherein the group of training scripts relating to the favorite workouts are synchronized with the user computing device by the device interface module during a synchronization operation.

2. The device of claim 1, wherein the user interface module determines one or more sensors employed by the user computing device and, wherein if it is determined that the user computing device does not have a first type of sensor required by the training script, the user interface module refrains from copying the training script to the user computing device during a synchronization operation.

3. The device of claim 2, wherein the user interface module provides for the user to enter identification data for the user computing device.

4. The device of claim 2, wherein the device includes a table correlating a user computing device identification with one or more sensors.

5. The device of claim 1, wherein the device transfers, during a synchronization operation, the one or more training scripts from a calendar interface associated with a user profile.

6. The device of claim 5, wherein the device is further operable to:
    determine the date of the synchronization operation;
    determine subsequent dates over a defined time period;
    associate a date tag to the one or more training scripts in the calendar interface during the defined time period; and
    transfer the one or more tagged training scripts to the user computing device during the synchronization operation.

7. The device of claim 1, wherein the device receives information from the user computing device during a synchronization operation relating to a performance of the training script by the user during the workout.

8. The device of claim 7, wherein the received information includes actual duration or intensity of activities within the training script that are performed by the user.

9. The device of claim 7, wherein the received information is associated with icons representing the one or more training scripts, for review by the user.

10. A device for creating a training script for a workout, comprising:
    a processor;
    a user interface for receiving input from one or more users; and memory storing computer readable instructions that, when executed, cause the device to:
prompt a user to input data, via the user interface, specifying a step in a training script;
creating one or more training steps to operate an other device to display a prompt for the one or more training steps;
determine one or more sensors employed by the other device;
compile the one or more training steps into a first training script;
store the first training script in a script database;
determine that the one or more sensors do not comprise a first type of sensor required by the first training script;
receiving, via the user interface, user input indicating a selection of one or more other training scripts;
synchronize the selected one or more other training scripts in the script database with the other device; and
refrain from copying the first training script to the other device when synchronizing the selected one or more other training scripts.

11. The device of claim 10, wherein the computer readable instructions, when executed, further cause the device to:
receive user input selections defining a user profile.

12. The device of claim 11, the user profile comprises a group of training scripts relating to favorite workouts, and wherein the computer readable instructions, when executed, further cause the device to:
synchronize, during a synchronization operation with the other device, the group of training scripts relating to favorite workouts.

13. The device of claim 10, wherein the computer readable instructions, when executed, further cause the device to synchronize the selected one or more training scripts by transferring the one or more training scripts from a calendar interface associated with a user profile.

* * * * *